US008623101B2

(12) United States Patent
Tateishi et al.

(10) Patent No.: US 8,623,101 B2
(45) Date of Patent: Jan. 7, 2014

(54) COLORING COMPOSITION, AZO COMPOUND AND INK

(71) Applicant: Fujifilm Corporation, Tokyo (JP)

(72) Inventors: Keiichi Tateishi, Kanagawa (JP); Yoshihiko Fujie, Kanagawa (JP); Youichirou Takeshima, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/930,318

(22) Filed: Jun. 28, 2013

(65) Prior Publication Data

US 2013/0284064 A1 Oct. 31, 2013

Related U.S. Application Data

(63) Continuation of application No. PCT/JP2011/079680, filed on Dec. 21, 2011.

(30) Foreign Application Priority Data

Dec. 28, 2010 (JP) .................. 2010-294320
Jun. 27, 2011 (JP) .................. 2011-142323

(51) Int. Cl.
C09B 67/22 (2006.01)
C09D 11/00 (2006.01)

(52) U.S. Cl.
USPC ............. 8/637.1; 8/638; 8/639; 8/570; 8/571; 8/573; 8/575; 106/31.01

(58) Field of Classification Search
USPC .......... 8/637.1, 638, 639, 570, 571, 573, 575; 106/31.01
See application file for complete search history.

(56) References Cited

U.S. PATENT DOCUMENTS

2004/0129172 A1  7/2004  Harada et al.
2011/0091696 A1  4/2011  Tanaka et al.

FOREIGN PATENT DOCUMENTS

| JP | 200483903 A | 3/2004 | |
| JP | 2005-225979 | * 8/2005 | ............. C09D 11/00 |
| JP | 2005225979 A | 8/2005 | |
| JP | 2005264085 A | 9/2005 | |
| JP | 2007224276 A | 9/2007 | |
| JP | 2009293016 A | 12/2009 | |
| JP | 2009298966 A | 12/2009 | |
| JP | 2010100796 A | 5/2010 | |

OTHER PUBLICATIONS

STIC Search Report dated Aug. 8, 2013.*
Written Opinion of the International Searching Authority issued Mar. 27, 2012 from the International Searching Authority in counterpart application No. PCT/JP2011/079680.

International Search Report issued Mar. 27, 2012 from the International Searching Authority in counterpart application No. PCT/JP2011/079680.
Translation of Written Opinion (PCT/ISA/237), issued by the International Searching Authority in counterpart International Patent Application No. PCT/JP2011/079680.
International Preliminary Report on Patentability (PCT/IB/373), dated Jul. 10, 2013, issued by the International Bureau in counterpart International Patent Application No. PCT/JP2011/079680.

* cited by examiner

Primary Examiner — Eisa Elhilo
(74) Attorney, Agent, or Firm — Sughrue Mion, PLLC

(57) ABSTRACT

There is provided a coloring composition containing at least a first coloring material and at least a second coloring material, in which the first coloring material is a compound represented by the following Formula (Y), the second coloring material is, for example, the following compound 8, and the mass ratio of the content (% by mass) of the second coloring material in the composition to the content (% by mass) of the first coloring material in the composition is 0.001 to 1.0.

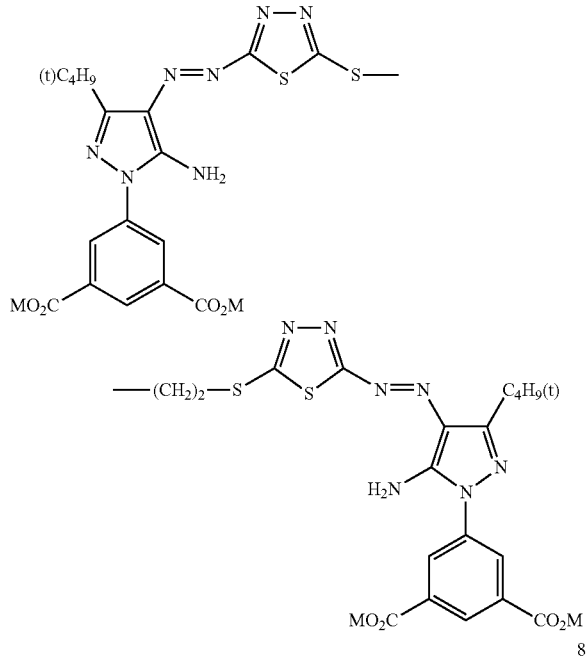

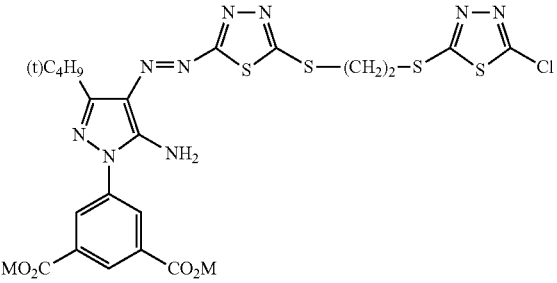

Formula (Y)
In Formula (Y), a plurality of M each independently represent a hydrogen atom or a cation, and when M represents a cation, M represents a $Li^+$ ion, a $Na^+$ ion, a $K^+$ ion or a $NH_4^+$ ion.

9 Claims, No Drawings

COLORING COMPOSITION, AZO COMPOUND AND INK

TECHNICAL FIELD

The present invention relates to a coloring composition, an azo compound and an ink.

BACKGROUND ART

As computers are spread, inkjet printers have been recently widely used for printing on, for example, paper, film, or fabric at home besides offices.

An inkjet recording method may be a manner of discharging liquid drops by applying pressure by a piezo element, a manner of discharging liquid drops by generating bubbles in an ink by heat, a manner using an ultrasonic wave, or a manner of absorptively discharging liquid drops by an electrostatic force. As an ink for inkjet recording, an aqueous ink, an oily ink, or a solid (melt type) ink is used. Among these inks, the aqueous ink is mainly used from the viewpoints of production, handling property, odor, safety, and the like.

A colorant used in the ink for the inkjet recording needs to ensure high solubility to a solvent, recording at a high concentration, favorable colors, excellent fastness to light, heat, air, water, or chemicals, good settlement to an image-receiving material, low spreading, excellent preservation as an ink, non-toxicity, high purity, and availableness at low price. However, it is very difficult to find a colorant satisfying the requirements at a high level.

In order to improve image preservation properties, particularly light fastness of an image, many suggestions have been conventionally made. For example, Patent Document 1 describes a coloring material (colorant) that may improve light fastness of an image and at the same time form an image with excellent color strength, especially, in a yellow ink having low light fastness of an image, among cyan, magenta and yellow inks. Also, Patent Document 2 describe a method of using an ink including a first coloring material with excellent image fastness, combined with a second coloring material having a different structure from the first coloring material so as to improve light fastness of an image, and form an image excellent in hue, and at the same time to suppress clogging of an ink supply path or improve storage stability.

RELATED ART

Patent Document

Patent Document 1: Japanese Patent Application Laid-Open No. 2004-083903
Patent Document 2: Japanese Patent Application Laid-Open No. 2009-293016

DISCLOSURE OF INVENTION

Problems to be Solved by the Invention

However, upon investigation by the present inventors, it has been found that even though the technologies described in the Patent Documents, as exemplified above, are used, the following problems still exist.

As a requirement for long-term storage preservation of an ink has been recently especially increased, it has been determined that in the use of the ink containing the coloring material described in Patent Document 1, there is a problem of the compatibility of a long-term storage stability of the ink and a concentration change of an inkjet recording image under high humidity. Also, upon investigation by the present inventors on the technology described in Patent Document 2, it has been determined that the second colorant having a similar structure to the first coloring material may significantly deteriorate inkjet image preservation properties (light fastness, ozone gas fastness, high-humidity preservation, heat fastness) depending on the kind or amount of the corresponding chemical structure.

Also, in an ink, there may exist impurities caused from remaining matters that cannot be removed during preparation of, for example, a coloring material, or there may be impurities which are thought to be eluted to the ink from a member constituting an ink cartridge or an ink supply path. Meanwhile, like Patent Document 2, there is generally known a method of using a structural analog of a colorant together with additives in an ink for the purpose of improving the characteristics of an inkjet ink (for example, adjustment of a liquid property, and improvement of an image preservation property). The material mixed with the ink may be a cause of clogging of an ink supply path, or reduction of an ink supply characteristic, and further ink storage stability, and thus, is considered as a problem to be solved from the viewpoint of reliability, especially, in the performance of recently required high-resolution recording. However, in general, it is difficult to remove such a material. Even if it can be removed, a considerably high cost is required. Accordingly, the addition of an excessive purification process may interrupt products from being supplied to users at a low cost, and may be a serious problem in practical use.

Accordingly, an object of the present invention is to provide a coloring composition and an azo compound useful in a yellow ink composition or an ink for inkjet recording, which may provide an image excellent in light fastness, ozone gas fastness and moisture fastness, and form an image excellent in hue, and at the same time may suppress clogging of an ink supply path or sufficiently satisfy storage stability.

Means for Solving the Problems

The aforementioned object is accomplished by the following inventions.

[1] A coloring composition containing at least a first coloring material and at least a second coloring material,
in which the first coloring material is a compound represented by the following Formula (Y), the second coloring material is at least one compound selected from the following Group A, and the mass ratio of the content (% by mass) of the second coloring material in the composition to the content (% by mass) of the first coloring material in the composition is 0.001 to 1.0.

Formula (Y)
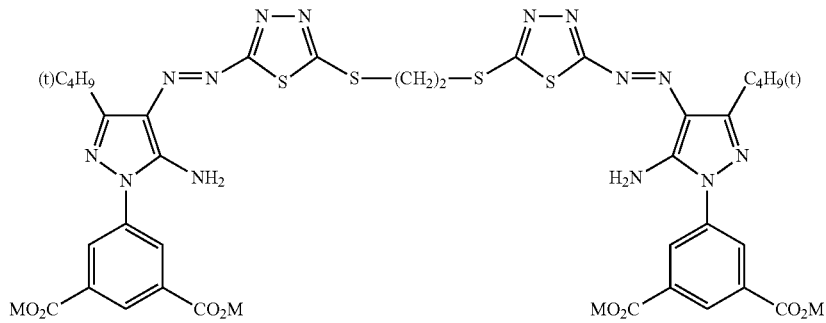
In Formula (Y), a plurality of M each independently represents a hydrogen atom or a cation, and when M represents a cation, M represents a Li⁺ ion, a Na⁺ ion, a K⁺ ion or a NH$_4^+$ ion.
Group A
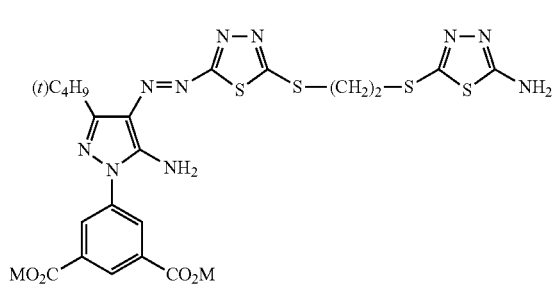
1
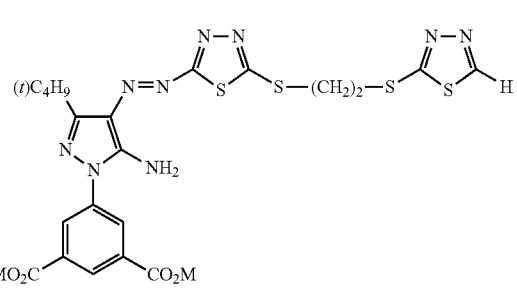
2
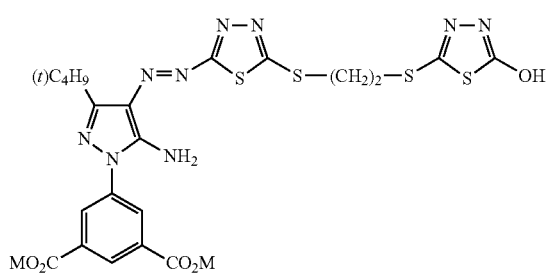
3
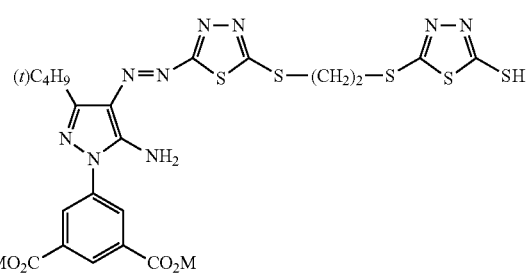
4
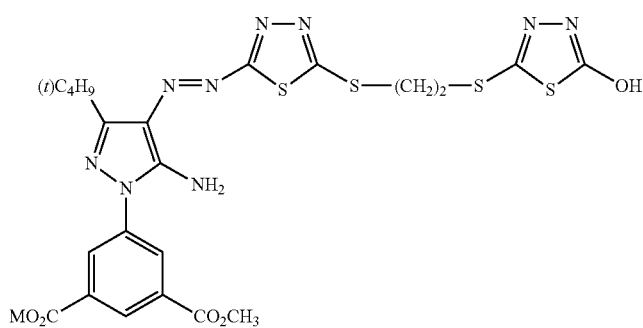
5

-continued

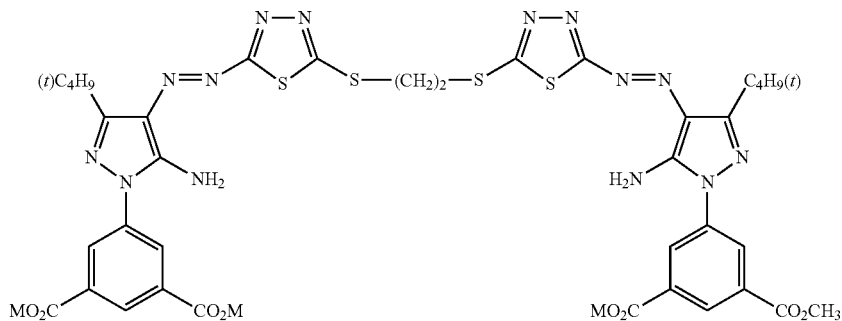

6

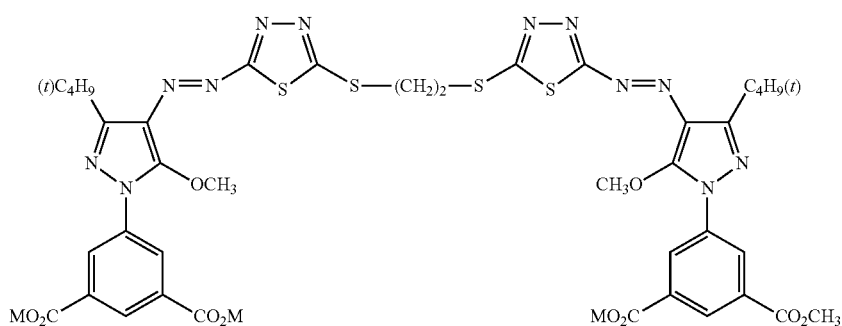

7

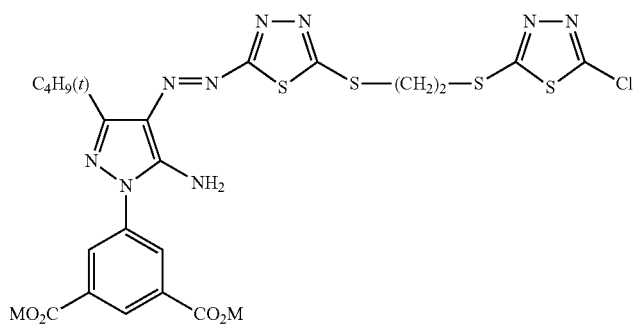

8

In Group A, a plurality of M each independently represents a hydrogen atom or a cation, and when M represents a cation, M represents a $Li^+$ ion, a $Na^+$ ion, a $K^+$ ion or a $NH_4^+$ ion.)

[2] The coloring composition of [1], in which the compound selected from the Group A is at least one kind selected from the compounds 1, 2, 3 and 8.

[3] The coloring composition of [1] or [2], in which a main component of M is a $K^+$ ion in the compound represented by Formula (Y), and a main component of M is a $K^+$ ion in the compound selected from the Group A.

[4] The coloring composition of any one of [1] to [3], in which M is a $K^+$ ion in both of the compound represented by Formula (Y) and the compound selected from the Group A.

[5] The coloring composition of any one of [1] to [4], in which the content (% by mass) of the first coloring material is 1% by mass to 15% by mass based on the total mass of the coloring composition.

[6] The coloring composition of any one of [1] to [5], in which the content (% by mass) of the first coloring material is 8% by mass to 12% by mass based on the total mass of the coloring composition.

[7] The coloring composition of any one of [1] to [6], in which the mass ratio of the content (% by mass) of the second coloring material in the coloring composition to the content (% by mass) of the first coloring material in the coloring composition is 0.001 to 0.2.

[8] The coloring composition of any one of [1] to [7], in which the content (% by mass) of the second coloring material is 0.01% by mass to 1.1% by mass based on the total mass of the coloring composition.

[9] A compound represented by the following Formula (Y-1).

Formula (Y-1)

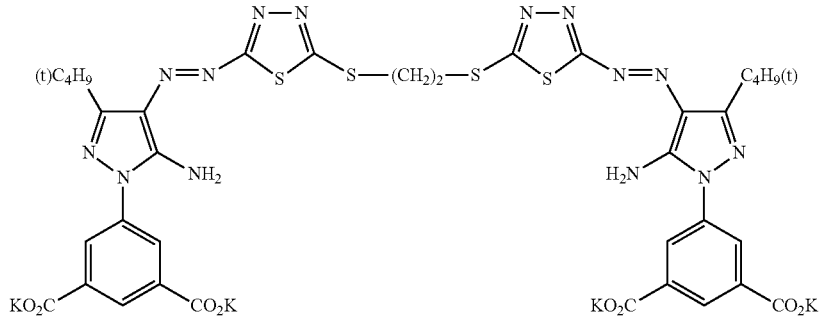

Effects of the Invention

According to the present invention, there may be provided a yellow coloring composition and a novel azo compound useful in the coloring composition, which may provide an image excellent in preservation properties (especially, light fastness, ozone gas fastness and moisture fastness), and further form an image excellent in hue, and at the same time may suppress clogging of an ink supply path or sufficiently satisfy storage stability.

EMBODIMENTS FOR CARRYING OUT THE INVENTION

Hereinafter, the present invention will be described in detail with reference to preferred embodiments.

Also, in the present invention, in the case where a compound is a salt, the salt is dissociated into ions to be present in a coloring composition and an ink using the coloring composition, but for the convenience of description, the expression "the salt is included" is used. The compound represented by Formula (Y-1) is a novel azo compound. The compound represented by Formula (Y) and the compound represented by Formula (Y-1) are useful in a coloring composition of the present invention. Also, in the following description, the compound represented by Formula (Y) or the compound represented by Formula (Y-1), as a first coloring material, will be abbreviatedly mentioned as "compound of Formula (Y)" or "compound of (Y-1)", respectively. Also, at least one kind compound selected from Group A, as a second coloring material, will be abbreviatedly mentioned described as "compound of Group A".

Based on the above described problems of the conventional technologies, the present inventors thought that a coloring material used for a yellow ink needs to be investigated in detail.

As described above, among respective yellow, magenta, and cyan inks widely used as inks for inkjet recording, especially, the yellow ink shows a tendency to be degraded in light fastness of a formed image. Accordingly, the present inventors carried out various investigations on the coloring material used for the yellow ink. As a result, they spotlighted that, especially, the compound of Formula (Y) below described in Patent Document 1, especially the compound of Formula (Y-1) below, is excellent in light fastness and color strength.

Also, the present inventors prepared a coloring composition containing only the compound of Formula (Y) as a coloring material, and an ink using the coloring material, and then investigated various images formed using the ink, clogging of an ink supply path, or storage stability. As a result, although the ink for inkjet recording, obtained using the coloring composition containing only the compound of Formula (Y) as the coloring material, has a performance exceeding a predetermined level, they concluded that the ink is still insufficient to satisfy recent high requirements, especially, in storage stability of the ink for inkjet recording. Especially, it was found that when an inkjet recording device was left for a long time without being used in a state where the ink was mounted in the inkjet recording device, a reduction in a discharging property or a reduction of storage stability of the ink occurred, depending on the inkjet recording device.

On these phenomena, the present inventors investigated in detail. After the inkjet recording device was left for a long time without being used in a state where the ink containing a high content of the compound of Formula (Y) was mounted in the inkjet recording device, it was observed through a recording head that foreign materials generated within a nozzle. As a result of investigation into the foreign materials, it was found that the materials were generated by crystal precipitation of a colorant. It was found that when the recording head in which such foreign materials generate is used, a discharging property is reduced and also storage stability of an ink is reduced by the foreign materials.

In other words, in an image formed using the ink containing the compound of Formula (Y), a conventional technology was insufficient to compatibly satisfy all performances such as an excellent image preservation property, an excellent color reproduction range, suppression of clogging of an ink supply path, and storage stability. More specifically, the conventional technology was insufficient to provide an ink that satisfies the following three performances at once. In conclusion, it is required to improve image fastness of a printed matter obtained using the ink containing the specific coloring material to satisfy a recent required high level, expand a red color reproduction range in an image formed by combination of the ink with a cyan or magenta ink, and also satisfy suppression of clogging of an ink supply path or storage stability.

In order to solve the aforementioned technical problems occurred when using the compound of Formula (Y), the present inventors have reviewed and implemented the present invention. That is, in the present invention, the aforementioned technical problems may be solved by the coloring composition and ink containing a compound represented by the following Formula (Y) as a first coloring material and at least one compound selected from the following Group A as a second coloring material in a specific mass ratio.
Formula (Y)
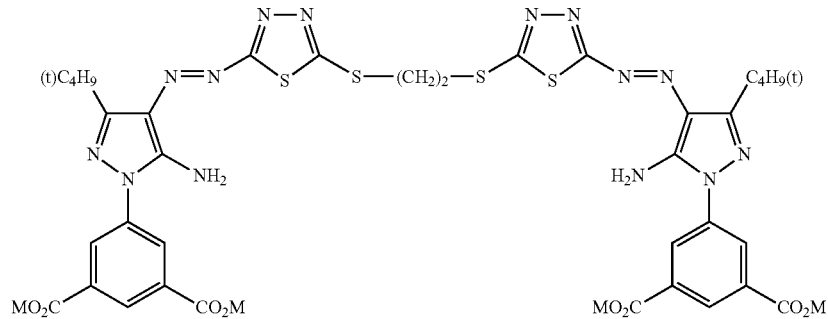
In Formula (Y), a plurality of M each independently represents a hydrogen atom or a cation, and when M represents a cation, M represents a $Li^+$ ion, a $Na^+$ ion, a $K^+$ ion or a $NH_4^+$ ion.
Group A
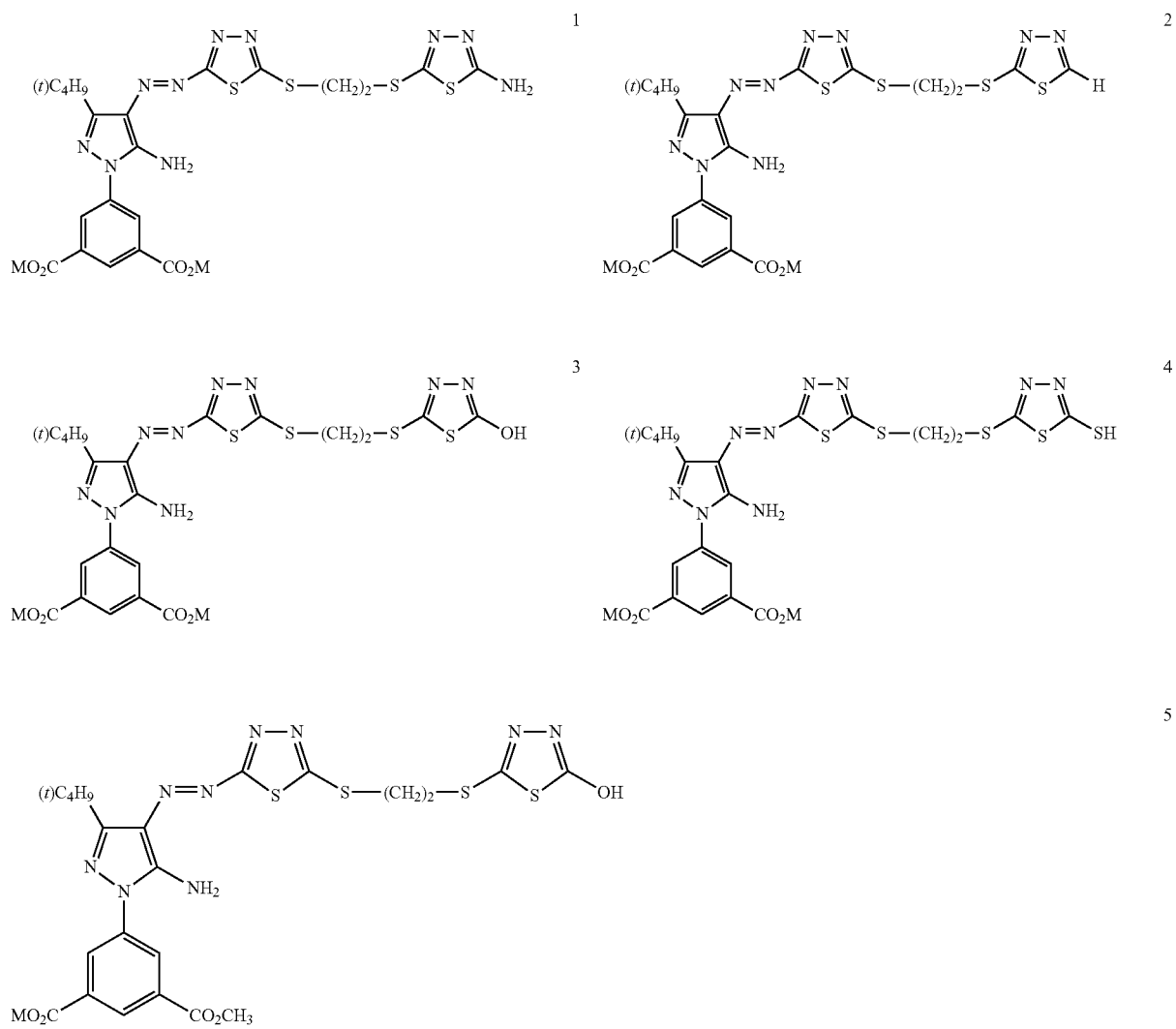

-continued

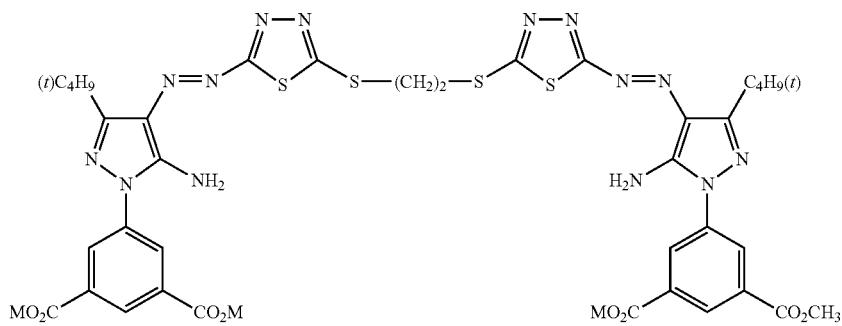

6

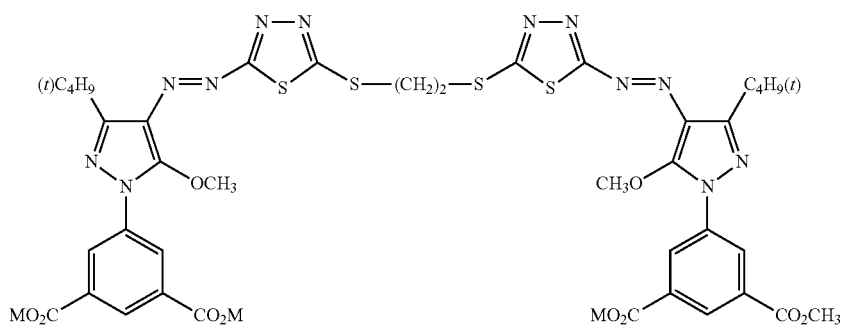

7

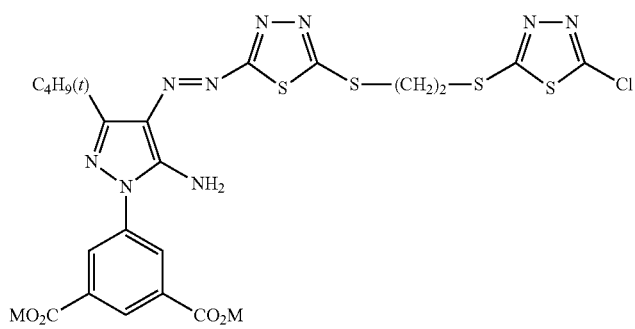

8

In Group A, a plurality of M each independently represents a hydrogen atom or a cation, and when M represents a cation, M represents a $Li^+$ ion, a $Na^+$ ion, a $K^+$ ion or a $NH_4^+$ ion.

In the present invention, it is particularly preferred that as the first coloring material, the compound represented by the following Formula (Y-1) is used, and at the same time, as the second coloring material, the compound 1, 2, 3, 5, 6 or 8 in the Group A is used. As the second coloring material, the compound 1, 2, 3, 6 or 8 is more preferable while being still more preferably the compound 1, 2, 3 or 8.

As described above, by combining coloring materials used in the coloring composition with a compound having a specific structure, and containing the coloring materials in the coloring composition in a specific mass ratio, it is possible to obtain the effects of the present invention (storage stability of ink, tinctorial strength of ink and image fastness) particularly remarkably. Hereinafter, the coloring composition of the present invention will be described in detail.

<Coloring Composition>

The coloring composition of the present invention may be used for an ink for inkjet recording.

Hereinafter, the components constituting the coloring composition and the ink for inkjet recording (hereinafter, simply referred to as ink in some cases) or the properties of the ink will be described in detail.

(Coloring Material)

[First Coloring Material: Compound Represented by Formula (Y) and Compound Represented by Formula (Y-1)]

The coloring composition of the present invention and the ink using the coloring composition are required to contain, as the first coloring material, the compound represented by the following Formula (Y) having characteristics that are excellent in tinctorial strength of storage stable inkjet recorded images and storage stability of inkjet recorded images.

Formula (Y)

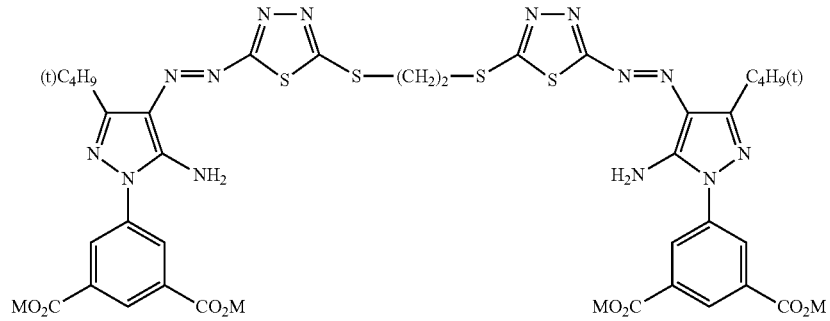

In Formula (Y), a plurality of M each independently represents a hydrogen atom or a cation, and when M represents a cation, M represents a $Li^+$ ion, a $Na^+$ ion, a $K^+$ ion or a $NH_4^+$ ion.

M represents a hydrogen atom, a $Li^+$ ion, a $Na^+$ ion, a $K^+$ ion or a $NH_4^+$ ion, particularly preferably a $Na^+$ ion, a $K^+$ ion or a $NH_4^+$ ion, still more preferably a $Na^+$ ion or a $K^+$ ion, and among them, most preferably a $K^+$ ion. In the dye represented by Formula (Y), it is preferred that at least one M is a $K^+$ ion, it is more preferred that the countercation, which is the main component of M, is a $K^+$ ion, and it is still more preferred that every M is a $K^+$ ion.

The dye represented by Formula (Y) may be in a form of a mixed salt in which multiple kinds of M are present. In the case of the mixed salt, it is preferred that 50% to 100%, more preferably 80% to 100%, particularly 90% to 100% of M is a $K^+$ ion in terms of the mole fraction in M possessed by the dye represented by Formula (Y) contained in an ink. Other than a $K^+$ ion, M is preferably a $Na^+$ ion or a $NH_4^+$ ion, and more preferably $Na^+$ ion.

Further, it is most preferred that every M in the dye represented by Formula (Y) contained in the coloring composition is a $K^+$ ion, besides a mixed salt. Since every M is a $K^+$ ion, in a molecular dispersion state when dissolved in an aqueous solution or an ink solution, cations are exchanged in an ionized state where a carboxyl group, which is an ionic hydrophilic group or a salt thereof ($—CO_2M$), is dissociated into $—CO_2^-$ and $M^+$. Therefore, it is possible to obtain an effect that a salt having lower solubility in an aqueous solution or an ink solution is formed, thereby easily suppressing precipitation in a form of a salt of a colorant.

Particularly, among the compound represented by Formula (Y), it is preferred to use the compound represented by Formula (Y-1).

Further, the present invention relates to a compound represented by the following Formula (Y-1).

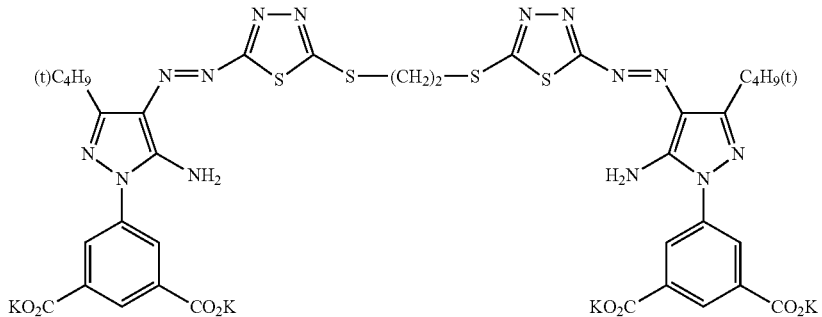

The dyes represented by Formula (Y) and Formula (Y-1) can be synthesized by a general synthesis. For example, the dyes can be synthesized in the same manner as the method described in [0066] and [0067] of Japanese Patent Application Laid-Open No. 2004-083903.

[Group A]

The coloring composition of the present invention is needed to be constituted by containing a second coloring material having characteristics that are excellent in storage stability of the coloring composition, tinctorial strength of the ink and image fastness of a printed matter, in addition to the compound of Formula (Y) or the compound of Formula (Y-1) used as the first coloring material as described above. In the present invention, the at least one compound selected from the following Group A is used as the second coloring material. Among at least one compound selected from the following Group A, it is preferred to use Compound 1, 2, 3, 5, 6 or 8 in Group A, it is more preferred to use Compound 1, 2, 3, 6 or 8, and it is still more preferred to use Compound 1, 2, 3 or 8.

In the present invention, at least one compound as the second coloring material selected from Group A may be used either alone or in combination of two or more thereof. In the present invention, it is preferred to use combination of Compounds 1, 2, 3, 5, 6 and 8, as the second coloring material, it is more preferred to use combination of Compounds 1, 2, 3, 6 and 8, and it is still more preferred to use combination of Compounds 1, 2, 3 and 8.

Further, the at least one compound selected from the following Group A exhibits a synergy effect when used in combination with the compound of Formula (Y), thereby providing the effects as follows. That is, by containing these coloring materials, it is possible to provide a yellow coloring composition having a high tinctorial strength, as well as to provide an image that is excellent in light fastness, and further, to satisfy suppression of clogging of an ink supply path or storage stability sufficiently. Hereinafter, these formulas will be described.

Group A

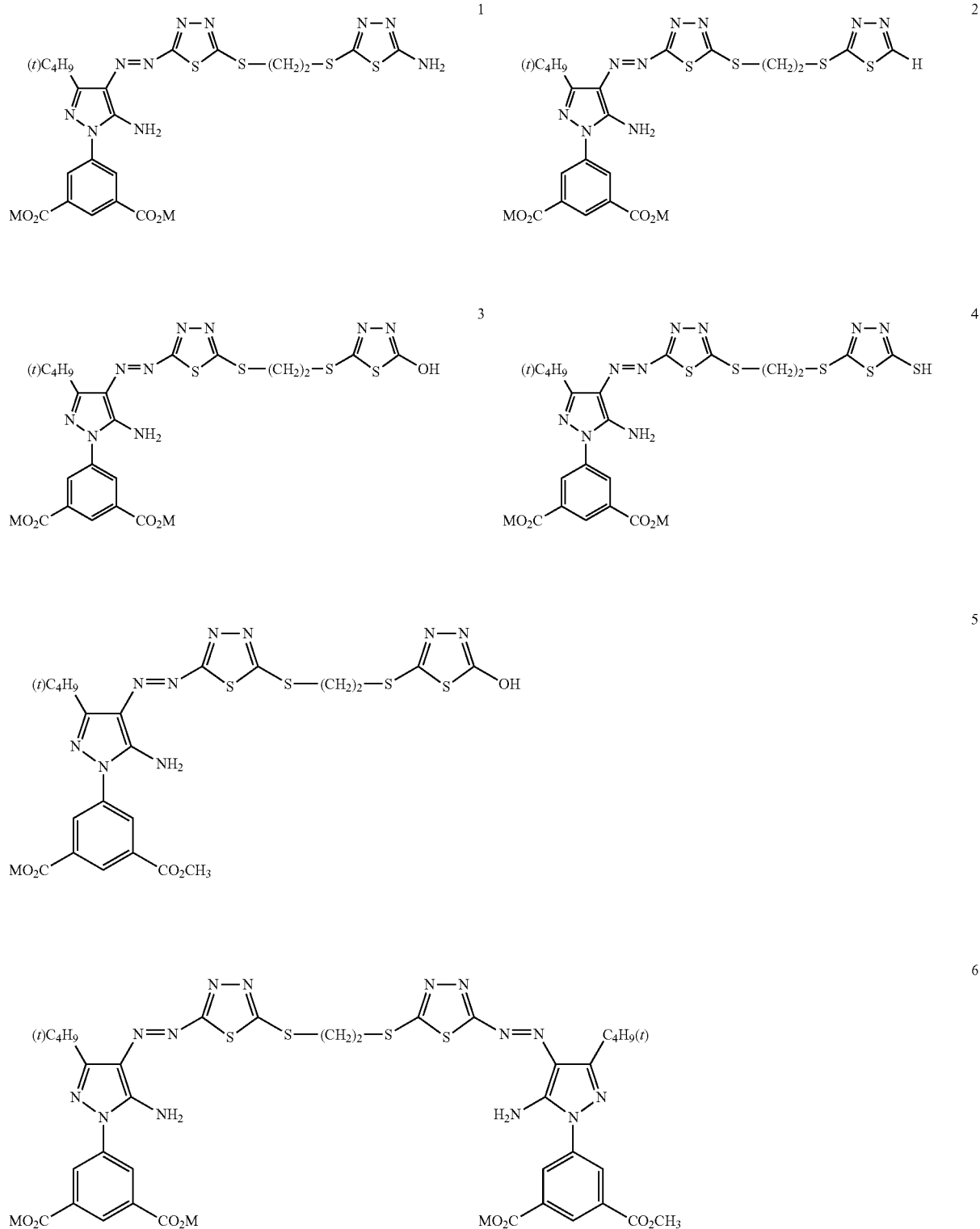

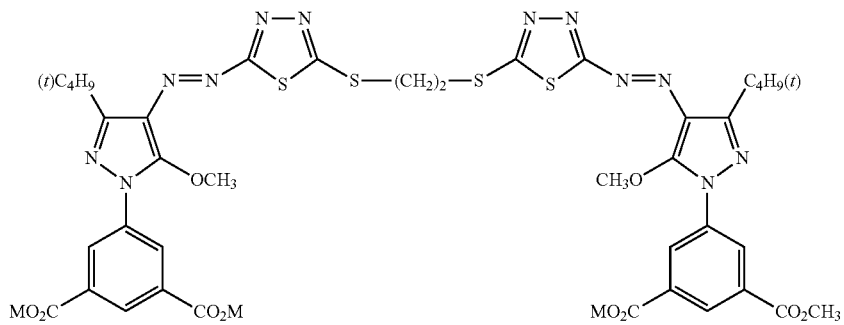

7

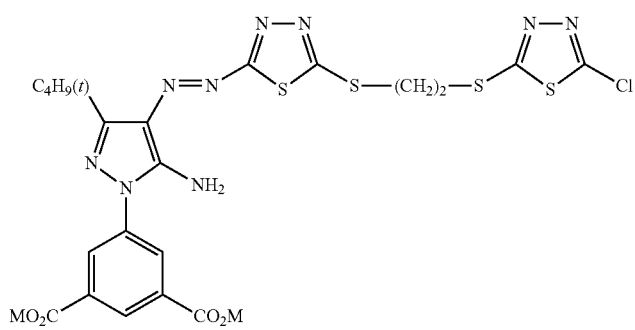

8

In Group A, a plurality of M each independently represents a hydrogen atom or a cation, and when M represents a cation, M represents a $Li^+$ ion, a $Na^+$ ion or a $NH_4^+$ ion.

In the at least one compound selected from Group A, a plurality of M represents a hydrogen atom, a $Li^+$ ion, a $Na^+$ ion, a $K^+$ ion or a $NH_4^+$ ion, preferably a $Na^+$ ion, a $K^+$ ion or a $NH_4^+$ ion, more preferably a $Na^+$ ion or a $K^+$ ion, and still more preferably a $K^+$ ion. In the at least one compound selected from the Group A, it is preferred that the countercation, which is the main component of M, is a $K^+$ ion, and it is more preferred that every M is a $K^+$ ion.

The at least one compound selected from the Group A may be in a form of a mixed salt in which multiple kinds of M are present. In the case of a mixed salt, it is preferred that 50% to 100%, more preferably 80% to 100%, still more preferably 90% to 100% of M is a $K^+$ ion in terms of the mole fraction in M possessed by the dye represented by Formula (Y) contained in an ink. Other than a $K^+$ ion, M is preferably a $Na^+$ ion or a $NH_4^+$ ion, and more preferably $Na^+$ ion.

Further, it is most preferred that every M in the compound selected from Group A contained in the coloring composition is a $K^+$ ion, besides a mixed salt. Since every M is a $K^+$ ion, in a molecular dispersion state when dissolved in an aqueous solution or an ink solution, cations are exchanged in an ionized state where a carboxyl group, which is an ionic hydrophilic group or a salt thereof (—$CO_2M$), is dissociated into —$CO_2^-$ and M. Therefore, it is possible to obtain an effect that a salt having lower solubility in an aqueous solution or an ink solution is formed, thereby easily suppressing precipitation in a form of a salt of a colorant.

The compound selected from the Group A can be synthesized by a general synthesis. For example, the compound can be synthesized in the same manner as the compound of Formula (Y) or Formula (Y-1) by changing the diazo component and its coupling component described in Japanese Patent Application Laid-Open No. 2004-083903 and combining them in various manners.

In the present invention, it is preferred that the main component of the countercation M in the compound represented by Formula (Y) is a $K^+$ ion, and the main component of the countercation M in the compound selected from the Group A is a $K^+$ ion as well. Herein, the main component of the countercation M refers to an ion constituting 80% or more, and preferably 90% in all the countercations M.

When the main component of the countercation M of the ionic hydrophilic group in the compound represented by Formula (Y) and the compound selected from Group A is a $K^+$ ion, the solubility in the coloring composition becomes higher, and the formation and precipitation of salt are suppressed, and thus, it is possible to enhance the storage stability of the coloring composition considerably.

Further, it is more preferred that every M in the compound represented by Formula (Y) and the compound selected from the Group A is a $K^+$ ion. Accordingly, it is possible to enhance the storage stability of the coloring composition considerably.

[Verification Method of Coloring Material]

For verification whether or not the coloring material used in the present invention is contained, it is possible to apply the following verification method including (1) to (3) using a liquid chromotography-mass spectrometry (LC-MS).

(1) a retention time of a peak, (2) a maximum absorption wavelength for the peak of (1), and (3) m/z (positive) and m/z (negative) of a mass spectrum for the peak of (1)

The analytical conditions of liquid chromotography-mass spectrometry are as follows. A liquid (ink) diluted about 1.000-fold with pure water was used as a sample for measurement. And, analysis was performed with liquid chromatography-mass spectrometry under the following conditions to measure a peak retention time and a peak having a measured Mass value.

Apparatus: Agilent 1100 (manufactured by Agilent Technologies, Inc.)

Column: YMC AM-312, inner diameter: 6.0 mm and length: 150 mm (manufactured by YMC Co., Ltd.)
Eluent: Liquid A: ultrapure water+0.1% acetic acid, 0.2% triethylamine Liquid B: methanol+0.1% acetic acid, 0.2% triethylamine
Mobile phase and gradient conditions: (Table 1)
In Table 1, "B. Conc." denotes a concentration of Liquid B.

TABLE 1

| | Time(min) | | | | | |
|---|---|---|---|---|---|---|
| | 0 | 3 | 10 | 30 | 35 | 60 |
| B. Conc. | 50 | 50 | 70 | 70 | 90 | 90 |

Flow rate: 1.0 mL/min
Detection wavelength: 210 nm to 600 nm
Column temperature in an oven: 40° C.

Further, the analytical conditions of mass spectrum are as follows. For the obtained peak, mass spectrum was measured under the following conditions, and the most strongly detected m/z was measured with respect to positive and negative, respectively.

Apparatus: Applied Biosystems™ QSTAR pulseri (manufactured by Life Technologies)
Ionization: ESI (positive)
Capillary voltage: 3.5 kV
Desolventizing gas: 300° C.
Ion source temperature: 120° C.
Detection method: TOF-MS
Detection range: 120 to 1500

Under the aforementioned method and conditions, measurement was performed on Compound (Y-1) of the first coloring material and Compounds 1 to 8 of Group A of the second coloring material (M=K$^+$) as representative examples for each coloring material. As a result, the obtained retention time and measured Mass value {m/z (positive)} are shown in Table 2. For coloring compositions and inks, measurement was performed under the same method and conditions as above. If the values correspond to those shown in Table 2, it can be considered that the compounds correspond to those used in the present invention.

Further, M may be verified by, for example, measurement by ion chromatography.

Measurement conditions of ion chromatography:
Apparatus: Personal Ion Analyzer PIA-1000 (manufactured by Shimadzu Corp.)
Column: Semi-micro column Shim-pack IC-C2 (S) for cation analysis (inner diameter: 100 mm and length: 2 mm)
Mobile phase: 2.5 mM aqueous oxalic acid solution
Column temperature: 35° C.
Flow rate: 0.2 mL/min

TABLE 2

| Coloring material | Retention time (min) | Measured Mass value (m/z) | Calculation Mass value (m/z) |
|---|---|---|---|
| 1 | 14.2 | (M + H)$^+$:607.1029 | (M + H)$^+$:C21H23N10O4S4 |
| 2 | 15.2 | (M + H)$^+$:592.0846 | (M + H)$^+$:C21H22N9O4S4 |
| 3 | 16.9 | (M + H)$^+$:608.0850 | (M + H)$^+$:C21H22N9O5S4 |
| 4 | 18.5 | N.D. | (M + H)$^+$:C19H21N7O4S3 |
| 5 | 21.8 | (M + H)$^+$:633.0862 | (M + H)$^+$:C22H21N10O5S4 |
| Y-1 | 24.4 | (M + H)$^+$:921.2026 | (M + H)$^+$:C36H37N14O8S4 |
| 7 | 36.7 | (M + H)$^+$:965.2286 | (M + H)$^+$:C39H41N12O10S4 |
| 6 | 38.2 | (M + H)$^+$:935.2134 | (M + H)$^+$:C37H39N14O8S4 |
| 8 | 24.8 | (M + H)$^+$:626.0218 | (M + H)$^+$:C21H21ClN9O4S4 |

TABLE 2-continued

[Content of Coloring Material]

The content (% by mass) of the first coloring material in the coloring composition is preferably 1% by mass to 15% by mass based on the total mass of the coloring composition. Further, the content (% by mass) of the first coloring material is also preferably 8% by mass to 12% by mass.

The coloring composition of the present invention may be a concentrated aqueous solution containing a colorant in a high concentration as an ink raw material. It is preferred that the concentration of the colorant in the thick aqueous solution is 15% by mass or less, and preferably 12% by mass or less from the viewpoint of the stability over time of the dye and the ease of handling, and 8% by mass or more from the viewpoint of enhancing the stability over time of the dye or reducing the transportation cost.

Further, the coloring composition of the present invention may be used for an ink composition or an inkjet ink. The concentration of the colorant in the inkjet ink is preferably 1% by mass to 12% by mass, more preferably 2% by mass to 8% by mass, and particularly preferably 3% by mass to 6% by mass from the viewpoint of the viscosity of the ink or the concentration of a printed matter.

The content of the second coloring material [at least one compound selected from Group A] is preferably set as follows. Specifically, the content (% by mass) of the second coloring material is preferably 0.001% by mass to 2.0% by mass, more preferably 0.005% by mass to 1.5% by mass, still more preferably 0.01% by mass to 1.1% by mass, and particularly preferably 0.05% by mass to 0.8% by mass based on the total mass of the coloring composition.

Further, with respect to other coloring materials, the content of the second coloring material in this case is more preferably set as follows. It is preferred that the content in the case of using any of the at least one compound selected from the Group A alone, and the total content in the case of using in combination of two or more selected from them are set so as to satisfy the aforementioned range, respectively. By setting the contents of the first coloring material and/or the second coloring material within the aforementioned range, it is possible to satisfy the light fastness and hue of images, as well as the reliability of the ink using the coloring composition, such as the storage stability and the recording durability.

Compound 1 in Group A is preferably contained in an amount of 0.001% by mass to 1.0% by mass, and more preferably 0.1% by mass to 1.0% by mass based on the total mass of the coloring composition.

Compound 2 in Group A is preferably contained in an amount of 0.003% by mass to 3.0% by mass, and more preferably 0.1% by mass to 3.0% by mass based on the total mass of the coloring composition.

Compound 3 in Group A is preferably contained in an amount of 0.001% by mass to 1.0% by mass, and more preferably 0.1% by mass to 1.0% by mass based on the total mass of the coloring composition.

Compound 4 in Group A is preferably contained in an amount of 0.0% by mass to 0.5% by mass based on the total mass of the coloring composition.

Compound 5 in Group A is preferably contained in an amount of 0.0% by mass to 0.5% by mass based on the total mass of the coloring composition.

Compound 6 in Group A is preferably contained in an amount of 0.0% by mass to 0.5% by mass based on the total mass of the coloring composition.

Compound 7 in Group A is preferably contained in an amount of 0.0% by mass to 0.5% by mass based on the total mass of the coloring composition.

Compound 8 in Group A is preferably contained in an amount of 0.002% by mass to 2.0% by mass, and more preferably 0.05% by mass to 2.0% by mass based on the total mass of the coloring composition.

Based on the total mass of the coloring composition, the mass ratio of the content (% by mass) of the second coloring material to the content (% by mass) of the first coloring material (the second coloring material/the first coloring material) is required to be 0.001 to 1.0.

Furthermore, in the present invention, the mass ratio of the content (% by mass) to the content (% by mass) of the first coloring material (the second coloring material/the first coloring material) is preferably 0.001 to 0.3. By setting the mass ratio of the contents of the coloring materials within the aforementioned range, it is possible to form an image having a high level of light fastness, which far surpasses the performance expected from the combination of the solubility and light fastness possessed by the first coloring material and the solubility and light fastness possessed by the second coloring material. Further, it is possible to obtain an image of more preferable hues. The mass ratio of the content (% by mass) of the second coloring material to the content (% by mass) of the first coloring material (the second coloring material/the first coloring material) is more preferably 0.001 to 0.2, still more preferably 0.01 to 0.2, and even still more preferably 0.02 to 0.12. By setting the mass ratio of the contents of the coloring materials within the aforementioned range, it is possible to form an image having an especially high level of light fastness even in the aforementioned mass ratio of the contents. Further, it is possible to obtain an image of particularly preferable hues, and it is also possible to satisfy the reliability as an ink.

If the mass ratio is 0.001 or more, the storage stability of the ink solution is enhanced, and if the mass ratio is 1.0 or less, the stability of the coloring composition in an aqueous solution is excellent. By setting the mass ratio of the contents of the coloring materials, it is possible to achieve an ink solution storage stability and an image fastness of printed matters at a high level, which surpasses the performance expected from the combination of the solubility and image fastness possessed by the first coloring material and the solubility and image fastness possessed by the second coloring material. Further, it is possible to obtain an image of preferable hues and satisfy the reliability as an ink.

The present inventors presume as follows on the reason that a synergy effect is exhibited by using the first coloring material and the second coloring material in a specific mass ratio, thereby compatibly combining impartment of the storage stability of an ink and the image fastness of printed matters. Since the first coloring material originally tends to have low solubility in a water-based medium, when an ink using the coloring composition containing these compounds is imparted to a recording medium, association or agglomeration of the coloring materials occurs rapidly immediately thereafter. The association or agglomeration tends to enhance the fastness of the coloring materials on the recording medium forming an image. On the other hand, however, excessive association or agglomeration may lower the solubility in an aqueous solution and an ink solution in some cases. In this regard, it is considered that, when the first coloring material and the second coloring material coexist, the first coloring material is formed in an optimum state of association or agglomeration with respect to light fastness, thereby enhancing the light fastness of an image.

Further, the present inventors presume as follows on the reason that a synergy effect is exhibited by using the first coloring material and the second coloring material in a specific mass ratio, thereby achieving the reliability of the ink using the coloring composition. As described above, there is a case where impurities, which are thought to be eluted from a member constituting an ink cartridge or an ink supply path, are incorporated into an ink, and cause clogging of the ink supply path, or reduction of an ink supply characteristic and further ink storage stability. The present inventors have reviewed, and as a result, have considered that, when a second coloring material having a similar structure to that of the first coloring material is coexistent in an ink, the tinctorial strength is not reduced, and the first coloring material can be suppressed from crystallization, thereby enhancing the storage stability of the ink considerably. That is, with respect to the reliability of the ink which could not be achieved by using the first coloring material alone as a coloring material, by combining the second coloring material, it is possible to obtain effects which surpass expectations, and achieve a sufficient reliability.

Further, the sum (% by mass) of the contents of the first coloring material and the second coloring material is preferably 1.00% by mass to 12.00% by mass, and particularly preferably 3.00% by mass to 8.0% by mass based on the total mass of the coloring composition. If the sum of the contents is 1.00% by mass or more, the light fastness and color strength are obtained sufficiently, and if the sum of the contents is 12.00% by mass or less, the inkjet discharging property is excellent, without precipitation of impurities in the ink.

Further, in the case where the coloring composition of the present invention is a yellow ink as an ink for inkjet recording, a preferable hue as a yellow ink has the following two meanings. That is, it means that an image formed by only a yellow ink is not tinged with red or green. Furthermore, in this connection, it means that, when forming a secondary colored image by using a yellow ink, that is a red or green image, the image has a hue not impaired in any of red and green color reproduction range.

[Ink for Inkjet Recording]

Hereinafter, an ink for inkjet recording, obtained using the coloring composition of the present invention, will be described.

The ink for inkjet recording (hereinafter, may be simply referred as "ink") may be prepared by dissolving and/or dispersing a coloring material 1 and a coloring material 2 of the present invention in a hydrophobic medium or an aqueous medium. The aqueous medium is preferably used for the ink. If necessary, other additives may be contained in a range not impairing the effects of the present invention. Other additives may be known additives such as a drying preventing agent (wetting agent), a discoloration preventing agent, an emulsion stabilizer, a permeation promoting agent, a UV absorbent, a preservative, a mycostat, a pH adjusting agent, a surface tension regulator, an antifoaming agent, a viscosity regulator, a dispersant, a dispersion stabilizer, a rust inhibitor, and a chelating agent. These various additives are directly added to an ink solution in the case of a water-soluble ink. In the case where an oil-soluble dye is used in a form of a dispersant, the additives are generally added to the dispersant after preparation of the dye dispersant, but may be added in an oil phase or an aqueous phase during the preparation.

The drying preventing agent is appropriately used for the purpose of suppressing an ink discharge hole of a nozzle used in an inkjet recording method from being clogged due to the dryness of the ink for inkjet.

As the drying preventing agent, a water-soluble organic solvent having vapor pressure lower than that of water is preferred. Specific examples thereof may include polyhydric alcohols represented by ethylene glycol, propylene glycol, diethylene glycol, polyethylene glycol, thiodiglycol, dithiodiglycol, 2-methyl-1,3-propanediol, 1,2,6-hexanetriol, an acetylene glycol derivative, glycerine and trimethylolpropane, lower alkyl ethers of polyhydric alcohol such as ethylene glycol monomethyl (or ethyl)ether, diethylene glycol monomethyl (or ethyl)ether and triethylene glycol monoethyl (or butyl)ether, heterocyclic rings such as 2-pyrrolidone, N-methyl-2-pyrrolidone, 1,3-dimethyl-2-imidazolidinone and N-ethylmorpholine, a sulfur-containing compound such as sulfolan, dimethylsulfoxide and 3-sulfolene, a polyfunctional compound such as diacetone alcohol and diethanol amine, and a urea derivative. Among them, polyhydric alcohol such as glycerine and diethylene glycol is more preferred. Further, the drying preventing agent may be used either alone or in combination of two kinds or more thereof. It is preferred that the drying preventing agent is contained in the ink in an amount of 10% by mass to 50% by mass.

The permeation promoting agent is appropriately used for the purpose of allowing the ink for inkjet to be permeated through paper well. As the permeation promoting agent, alcohols such as ethanol, isopropanol, butanol, di(tri)ethylene glycol monobutylether and 1,2-hexanediol, sodium lauryl sulfate, sodium oleate, a non-ionic surfactant or the like may be used. If the aforementioned permeation promoting agent is included in the ink in an amount of 5% by mass to 30% by mass, there is generally a sufficient effect, and it is preferred to use the permeation promoting agent in the range of the addition amount not causing spreading of print and printthrough of paper.

The UV absorbent is used for the purpose of improving a preservation property of an image. As the UV absorbent, a compound absorbing UV to emit fluorescence, that is, a socalled fluorescent brightening agent, may be used which is represented by a benzotriazole-based compound described in Japanese Patent Application Laid-Open Nos. S58-185677, 561-190537, H2-782, H5-197075 and H9-34057, a benzophenone-based compound described in Japanese Patent Application Laid-Open Nos. S46-2784 and H5-194483, and U.S. Pat. No. 3,214,463, a cinnamic acid-based compound described in Japanese Patent Publication Nos. S48-30492 and S56-21141, and Japanese Patent Application Laid-Open No. H10-88106, a triazine-based compound described in Japanese Patent Application Laid-Open Nos. H4-298503, H8-53427, H8-239368 and H10-182621, and Japanese Publication of International Patent Application No. H8-501291, a compound described in Research Disclosure No. 24239, or a stilbene-based or benzooxazole-based compound.

The discoloration preventing agent is used for the purpose of improving a preservation property of an image. As the discoloration preventing agent, various kinds of organic and metal complex-based discoloration preventing agents may be used. Examples of the organic discoloration preventing agent may include hydroquinones, alkoxyphenols, dialkoxyphenols, phenols, anilines, amines, indanes, cromanes, alkoxyanilines, heterocyclics and the like, and examples of the metal complex may include a nickel complex, a zinc complex and the like. More specifically, examples thereof may include compounds included in the formula and the compound examples of a compound described in the patent documents cited in Paragraphs I to J of VII of Research Disclosure No. 17643, Research Disclosure No. 15162, the left column on page 650 of Research Disclosure No. 18716, page 527 of Research Disclosure No. 36544, page 872 of Research Disclosure No. 307105 and Research Disclosure No. 15162, or a representative compound described on pages 127 to 137 of Japanese Patent Application Laid-Open No. S62-215272.

The mycostat may be sodium dehydroacetate, sodium benzoate, sodium pyridinethione-1-oxide, p-hydroxybenzoate ethyl ester, 1,2-benzisothiazolin-3-one or a salt thereof. These may be preferably used in the ink in an amount of 0.02% by mass to 1.00% by mass.

As the pH adjusting agent, inorganic acid such as hydrochloric acid, sulfuric acid or phosphoric acid, organic acid such as acetic acid or benzoic acid, hydroxide such as sodium hydroxide or potassium hydroxide, halide such as ammonium chloride, sulfate such as sodium sulfate, carbonate such as potassium carbonate, potassium bicarbonate, or sodium hydrogen carbonate, phosphate such as sodium hydrogen phosphate or sodium dihydrogen phosphate, organic acid salt such as ammonium acetate or sodium benzoate, and various organic amines such as tributylamine or triethanolamine may be used. Especially, from the viewpoints of discharge stability and storage stability of the ink for inkjet, a pH adjusting agent having a buffer action is preferred, and potassium bicarbonate or potassium carbonate is preferably used. Potassium bicarbonate or potassium carbonate is more preferred. The use of the pH adjusting agent having the buffer action may suppress a pH change of the ink solution for inkjet with the elapse of time, and thus may solve problems such as discharge poorness of the ink caused by an increase in viscosity of the ink solution due to a decrease of pH of the ink solution, and decomposition of a dye with the elapse of time due to an increase of pH.

Also, the pH adjusting agent is added so that pH of the ink preferably ranges from 6 to 10, and more preferably ranges from pH 7 to 10. By the range of pH of the ink solution, the storage stability of the ink becomes better.

Also, the pH adjusting agent is appropriately used for the purpose of suppressing pH of the coloring composition of the present invention, besides inkjet, from being changed with the elapse of time.

The surface tension regulator may be a non-ionic, cationic or anionic surfactant. Also, the surface tension of the ink for inkjet of the present invention preferably ranges from 25 mN/m to 70 mN/m, and more preferably ranges from 25 mN/m to 60 mN/m. Also, the viscosity of the ink for inkjet recording of the present invention is preferably 30 mPa·s or less, and is more preferably adjusted to 20 mPa·s or less. Examples of the surfactant preferably include an anionic surfactant such as a fatty acid salt, an alkyl ester sulfate salt, an alkylbenzene sulfonate salt, an alkylnaphthalene sulfonate salt, a dialkyl sulfosuccinate salt, an alkyl ester phosphate salt, a naphthalene sulfonic acid formaline condensate and a polyoxyethylenealkyl ester sulfate salt, or a non-ionic surfactant such as polyoxyethylenealkylether, polyoxyethylenealkylallylether, polyoxyethylene fatty acid ester, sorbitan fatty acid ester, polyoxyethylene sorbitan fatty acid ester, polyoxyethylenealkylamine, glycerine fatty acid ester and an oxyethyleneoxypropylene block copolymer. Further, SURFYNOLS (AirProducts & Chemicals, Co., Ltd.) that is an acetylene-based polyoxyethylene oxide surfactant is preferably used. Further, an amine oxide type ampholytic surfactant such as N,N-dimethyl-N-alkylamine oxide is preferred. Moreover, a matter exemplified as a surfactant on pp. 37 to 38 of Japanese Patent Application Laid-Open No. S59-157,636 and Research Disclosure No. 308119 (1989) may be used.

As the antifoaming agent, a fluorine-based or silicon-based compound, a chelating agent represented by EDTA, or the like may be used if necessary.

In the case where the coloring material 1 and the coloring material 2 of the present invention are dispersed in an aqueous medium, it is preferred that coloring fine particles containing a colorant and an oil-soluble polymer are dispersed in the aqueous medium as described in Japanese Patent Application Laid-Open No. H11-286637, Japanese Patent Application Nos. H2000-78491, H2000-80259 and H2000-62370, or the compound of the present invention dissolved in a high boiling point organic solvent is dispersed in the aqueous medium as described in Japanese Patent Application Nos. H2000-78454, H2000-78491, H2000-203856 and H2000-203857. In the case where the compound of the present invention is dispersed in the aqueous medium, a specific method, the kinds of an oil-soluble polymer, a high boiling point organic solvent, and additives used therein, and the amounts thereof may preferably refer to the description in the aforementioned patent documents. Otherwise, the compound of the present invention may be dispersed in a solid fine particle state. In the dispersion, a dispersant or a surfactant may be used. As a dispersion device, a simple stirrer or impeller agitation type, an inline agitation type, a mill type (for example, a colloid mill, a ball mill, a sand mill, an attritor, a roll mill or an agitator mill), an ultrasonic type, and a high pressure emulsification and dispersion type (high pressure homogenizer; Goehring homogenizer, microfluidizer, DeBEE2000 or the like as a specific commercially-available device) may be used. The aforementioned method of preparing the ink for inkjet recording is described in detail in Japanese Patent Application Laid-Open Nos. H5-148436, H5-295312, 1-17-97541, H7-82515, H7-118584 and H11-286637, and Japanese Patent Application No. 2000-87539, in addition to the aforementioned patent documents, and may be used for preparing the ink for inkjet recording of the present invention.

As the aqueous medium, a mixture that contains water as a main component, and if necessary, is added with a water-miscible organic solvent may be used. Examples of the water-miscible organic solvent may include alcohol (for example, methanol, ethanol, propanol, isopropanol, butanol, isobutanol, sec-butanol, t-butanol, pentanol, hexanol, cyclohexanol and benzylalcohol), polyhydric alcohols (for example, ethylene glycol, diethylene glycol, triethylene glycol, polyethylene glycol, propylene glycol, dipropylene glycol, polypropylene glycol, butylene glycol, hexanediol, pentanediol, glycerine, hexanetriol and thiodiglycol), a glycol derivative (for example, ethylene glycol monomethyl ether, ethylene glycol monoethyl ether, ethylene glycol monobutyl ether, diethylene glycol monomethyl ether, diethylene glycol monobutyl ether, propylene glycol monomethyl ether, propylene glycol monobutyl ether, dipropylene glycol monomethyl ether, triethylene glycol monomethyl ether, ethylene glycol diacetate, ethylene glycol monomethyl ether acetate, triethylene glycol monomethyl ether, triethylene glycol monoethyl ether and ethylene glycol monophenyl ether), amine (for example, ethanolamine, diethanolamine, triethanolamine, N-methyldiethanolamine, N-ethyldiethanolamine, morpholine, N-ethylmorpholine, ethylenediamine, diethylenetriamine, triethylenetetramine, polyethyleneimine and tetramethylpropylenediamine), and other polar solvents (for example, formamide, N,N-dimethylformamide, N,N-dimethylacetamide, dimethylsulfoxide (DMSO), sulfolane, 2-pyrrolidone, N-methyl-2-pyrrolidone, N-vinyl-2-pyrrolidone, 2-oxazolidone, 1,3-dimethyl-2-imidazolidinone, acetonitrile and acetone). Meanwhile, the water-miscible organic solvent may be used in combination of two or more thereof.

In 100 parts by mass of the ink of the present invention, the coloring material 1 and the coloring material 2 of the present invention are contained preferably in an amount of 0.1 parts by mass to 20 parts by mass. Also, in the ink for inkjet of the present invention, the compound of the present invention may be used in combination with other colorants. When two or more kinds of colorants are used in combination, the total content of the colorants is preferably within the aforementioned range.

The ink of the present invention preferably has a viscosity of 40 cp or less. Also, the surface tension thereof preferably ranges from 20 mN/m to 70 mN/m. The viscosity and the surface tension may be adjusted by addition of various kinds of additives, such as, for example, a viscosity regulator, a surface tension regulator, a specific fastness adjusting agent, a film regulator, a UV absorbent, an antioxidant, a discoloration preventing agent, a mycostat, a rust inhibitor, a dispersant and a surfactant.

The ink of the present invention may be used to form a monochromic image or form an image of a full color. In order to form the full color image, a magenta hue ink, a cyan hue ink and a yellow hue ink may be used, and also a black hue ink may be further used so as to set up hues.

As an applicable yellow dye, predetermined matters may be used. Examples thereof may include an aryl or heterylazo dye having heterocyclic rings such as phenols, naphthols, anilines, pyrazolone or pyridones, chain-opening active methylene compounds, or the like as a coupling component (hereinafter, referred to as "coupler component"); an azomethine dye having chain-opening active methylene compounds or the like as a coupler component; a methine dye such as a benzylidene dye or a monomethineoxonol dye; and a quinine-based dye such as a naphthoquinone dye and an anthraquinone dye. Examples of other kinds of the dye may include a quinophthalon dye, a nitro and nitroso dye, an acridine dye, an acrydinone dye and the like.

As an applicable magenta dye, predetermined matters may be used. Examples thereof may include an aryl or heterylazo dye having phenols, naphthols, anilines or the like as a coupler component; an azomethine dye having pyrazolones, pyrazolotriazoles or the like as a coupler component; a methine dye such as an arylidene dye, a styryl dye, a melocyanine dye, a cyanine dye and an oxonol dye; a carbonium dye such as a diphenylmethane dye, a triphenylmethane dye and a xanthene dye, a quinone-based dye such as naphthoquinone, anthraquinone and anthrapyridone, and a condensed polycyclic ring-based dye such as a dioxazine dye.

As an applicable cyan dye, predetermined matters may be used. Examples thereof may include an aryl or heterylazo dye having phenols, naphthols, anilines or the like as a coupler component; an azomethine dye having heterocyclic rings such as phenols, naphthols, and pyrrolotriazoles, or the like as a coupler component; a polymethine dye such as a cyanine dye, an oxonol dye and a melocyanine dye; a carbonium dye such as a diphenylmethane dye, a triphenylmethane dye and a xanthene dye; a phthalocyanine dye; an anthraquinone dye; indigo and thioindigo dyes and the like.

Each of the aforementioned dyes may be a matter in which a portion of chromophore is dissociated to initially have each color of yellow, magenta and cyan, and in this case, the countercation may be an inorganic cation such as alkali metal or ammonium, an organic cation such as pyridinium or a quaternary ammonium salt, or a polymer cation having the aforementioned cations as a partial structure. Examples of an applicable black coloring material may include a dispersing element of carbon black besides disazo, trisazo and tetrazo dyes.

[Inkjet Recording Method]

The inkjet recording method of the present invention donates energy to the ink, and forms an image on known image-receiving materials, that is, plain paper, resin-coated paper, exclusive inkjet paper described in, for example, Japanese Patent Application Laid-Open Nos. H8-169172, H8-27693, H2-276670, H7-276789, H9-323475, S62-238783, H10-153989, H10-217473, H10-235995, H10-337947, H10-217597, and H10-337947, film, paper for use in electrophotography, fabric, glass, metal, ceramic, or the like.

When an image is formed, a polymer fine particle dispersion (also known as polymer latex) may be used in combination in order to impart a glossiness or a water fastness, or improve a weather fastness. The polymer latex may be added to the image-receiving material before, after or simultaneously with application of a colorant, and accordingly, may be added into image-receiving paper, or an ink, or used alone as a liquid. Specifically, the methods described in Japanese Patent Application Nos. 2000-363090, 2000-315231, 2000-354380, 2000-343944, 2000-268952, 2000-299465, and 2000-297365, and the like may be preferably used.

Hereinafter, the recording paper and the recording film used to perform inkjet printing by using the ink of the present invention will be described. In the recording paper and the recording film, a support is formed of a chemical pulp such as LBKP and NBKP, a mechanical pulp such as GP, PGW, RMP, TMP, CTMP, CMP and CGP, a used-paper pulp such as DIP, or the like, and, if necessary, a matter manufactured by various kinds of devices such as a fourdrinier machine and a rotoformer machine by mixing additives known in the art, such as a pigment, a binder, a sizing agent, a settlement agent, a cationic agent, and a strength additive for paper, may be used. In addition to the aforementioned support, any matter of a synthetic paper and a plastic film sheet may be used, and it is preferred that the thickness of the support ranges from 10 μm to 250 μm, and the basis weight thereof ranges from 10 $g/m^2$ to 250 $g/m^2$.

The support may be provided with an ink-receiving layer and a back coat layer at once, or may be provided with an ink-receiving layer and a back coat layer after a size press or an anchor coat layer is fanned by starch, polyvinyl alcohol or the like. Further, the support may be subjected to planarization treatment by a calendar device such as a machine calendar, a TG calendar, and a soft calendar. In the present invention, paper and plastic films in which polyolefins (for example, polyethylene, polystyrene, polyethylene terephthalate, polybutene, and a copolymer thereof) are laminated on both surfaces thereof are more preferably used as the support. It is preferred that a white pigment (e.g., titanium oxide or zinc oxide) or a coloring dye (e.g., cobalt blue, navy blue or neodymium oxide) is added to polyolefins.

The ink-receiving layer formed on the support contains a pigment or an aqueous binder. As the pigment, a white pigment is preferred, and examples of the white pigment may include an inorganic white pigment such as calcium carbonate, kaolin, talc, clay, diatomite, synthetic amorphous silica, aluminum silicate, magnesium silicate, calcium silicate, aluminum hydroxide, alumina, lithopone, zeolite, barium sulfate, calcium sulfate, titanium dioxide, zinc sulfide and zinc carbonate, and an organic pigment such as a styrene-based pigment, an acrylic pigment, a urea resin and a melamine resin. As the white pigment contained in the ink-receiving layer, a porous inorganic pigment is preferred, and in particular, for example, synthetic amorphous silica having a large fine pore area is appropriate. As the synthetic amorphous silica, any of silicic acid anhydride obtained by a dry manufacturing method and water-containing silicic acid obtained by a wet manufacturing method may be used. In particular, water-containing silicic acid is preferably used.

Examples of the aqueous binder contained in the ink-receiving layer may include a water-soluble polymer such as polyvinyl alcohol, silanol denatured polyvinyl alcohol, starch, cationic starch, casein, gelatin, carboxymethyl cellulose, hydroxyethyl cellulose, polyvinylpyrrolidone, polyalkylene oxide and a polyalkylene oxide derivative, and a water dispersible polymer such as a styrenebutadiene latex and an acryl emulsion. The aqueous binder may be used either alone or in combination of two kinds or more thereof. In the present invention, among them, polyvinyl alcohol or silanol denatured polyvinyl alcohol is particularly suitable from the viewpoints of the attachment property to the pigment and the stripping fastness of an ink-receiving layer. The ink-receiving layer may contain a mordant, an insolubilizer, a light fastness improving agent, a surfactant or other additives in addition to the pigment and the aqueous binder.

It is preferred that the mordant to be added to the ink-receiving layer is immobilized. To this end, a polymer-mordant is preferably used. The polymer-mordant is described in Japanese Patent Application Laid-Open Nos. S48-28325, S54-74430, S54-124726, S55-22766, S55-142339, S60-23850, S60-23851, S60-23852, S60-23853, S60-57836, S60-60643, 560-118834, S60-122940, S60-122941, S60-122942, S60-235134 and H1-161236, and U.S. Pat. Nos. 2,484,430, 2,548,564, 3,148,061, 3,309,690, 4,115,124, 4,124,386, 4,193,800, 4,273,853, 4,282,305 and 4,450,224. An image-receiving material including the polymer-mordant described on pages 212 to 215 of Japanese Patent Application Laid-Open No. H1-161236 is particularly preferred. If the polymer-mordant described in the aforementioned patent document is used, an image having an excellent image quality may be obtained, and at the same time, the light fastness of the image is improved.

The insolubilizer is effective to insolubilization of the image, and it is particularly preferred that the insolubilizer is a cation resin. The cation resin may be polyamidepolyamineepichlorohydrin, polyethyleneimine, polyaminesulfone, dimethyldiallylammonium chloride polymer, cation polyacrylamide, colloidal silica or the like. Among the cation resins, polyamidepolyamineepichlorohydrin is particularly appropriate. The content of the cation resin is preferably 1% by mass to 15% by mass and particularly preferably 3% by mass to 10% by mass based on the total solid of the ink-receiving layer.

Examples of the light fastness improving agent may include zinc sulfide, zinc oxide, hindered amine-based antioxidant, a benzophenone-based or benzotriazole-based UV absorbent, and the like. Among them, zinc sulfide is particularly appropriate.

The surfactant serves as a coating aid, a stripping improving agent, a slipping preventing agent or an antistatic agent. The surfactant is described in Japanese Patent Application Laid-Open Nos. S62-173463 and S62-183457. An organic fluoro compound may be used instead of the surfactant. It is preferred that the organic fluoro compound is hydrophobic. Examples of the organic fluoro compound include a fluorine-based surfactant, an oil phase fluorine-based compound (for example, fluorine oil), and a solid type fluorine compound resin (for example, a tetrafluoroethylene resin). The organic fluoro compound is described in Japanese Patent Publication No. S57-9053 (8th to 17th columns), and Japanese Patent Application Laid-Open Nos. S61-20994 and S62-135826. Examples of other additives to be added to the ink-receiving layer may include a pigment dispersant, a thickener, an antifoaming agent, a dye, a fluorescent brightening agent, a preservative, a pH adjusting agent, a matting agent, a hardening agent and the like. Also, the ink-receiving layer may have one layer or two layers.

The back coat layer may be provided into the recording paper and the recording film, and the component that may be added to the layer may be a white pigment, a water-based binder or other components. Examples of the white pigment that may be contained in the back coat layer may include a white inorganic pigment such as precipitated calcium carbonate, ground calcium carbonate, kaolin, talc, calcium sulfate, barium sulfate, titanium dioxide, zinc oxide, zinc sulfide, zinc carbonate, satin white, aluminum silicate, diatomite, calcium silicate, magnesium silicate, synthetic amorphous silica, colloidal silica, colloidal alumina, pseudo boehmite, aluminum hydroxide, alumina, lithopone, zeolite, hydrate halloysite, magnesium carbonate and magnesium hydroxide, an organic pigment such as a styrene-based plastic pigment, an acrylic plastic pigment, polyethylene, microcapsules, a urea resin and a melamine resin, and the like.

Examples of the water-based binder that may be contained in the back coat layer may include a water-soluble polymer such as a styrene/maleate copolymer, a styrene/acrylate copolymer, polyvinyl alcohol, silanol-modified polyvinyl alcohol, starch, cationic starch, casein, gelatin, carboxymethyl cellulose, hydroxyethyl cellulose and polyvinylpyrrolidone, a water-dispersible polymer such as a styrenebutadiene latex and an acryl emulsion, and the like. Examples of the other components that may be contained in the back coat layer may include an antifoaming agent, a defoaming agent, a dye, a fluorescent brightening agent, a preservative, an insolubilizer and the like.

Polymer latex may be added to a constitutional layer (including the back coat layer) of the inkjet recording paper and the recording film. Polymer latex is used for the purpose of improvement in physical properties of the layer, such as dimensional stabilization, curling prevention, attachment prevention, and crack prevention of the layer. Polymer latex is described in Japanese Patent Application Laid-Open Nos. S62-245258, S62-136648 and S62-110066. When polymer latex having a low glass transition temperature (40° C. or less) is added to the layer including the mordant, cracks or curling of the layer may be prevented. Further, even though polymer latex having a high glass transition temperature is added to the back coat layer, curling may be prevented.

The inkjet recording method using the ink of the present invention is not limited, and is used in a known manner, for example, a charge control manner discharging an ink using electrostatic force, a drop-on-demand manner (pressure pulse manner) using vibration pressure of a piezo element, a sound inkjet manner discharging an ink using radiation pressure by changing an electric signal into a sound beam and radiating the beam to the ink, a thermal inkjet manner using pressure generated by heating an ink to form bubbles, and the like. In the inkjet recording method, a manner of injecting an ink that is called a photo ink at a low concentration in a plurality of small volumes, a manner of improving an image quality by using a plurality of inks having substantially the same color and different concentrations, and a manner of using a colorless transport ink are included.

EXAMPLES

Synthesis Examples

Hereinafter, the synthesis method of a dye mixture of the present invention will be described in detail by the Examples but the present invention is not limited by the Examples.

A dye represented by Formula (Y-1) of the present invention may be induced by, for example, the following synthesis route.

In the following Examples, λmax indicates a maximum absorption wavelength, and εmax indicates a molar absorptivity in the maximum absorption wavelength. Also, simply described % indicates % by mass.

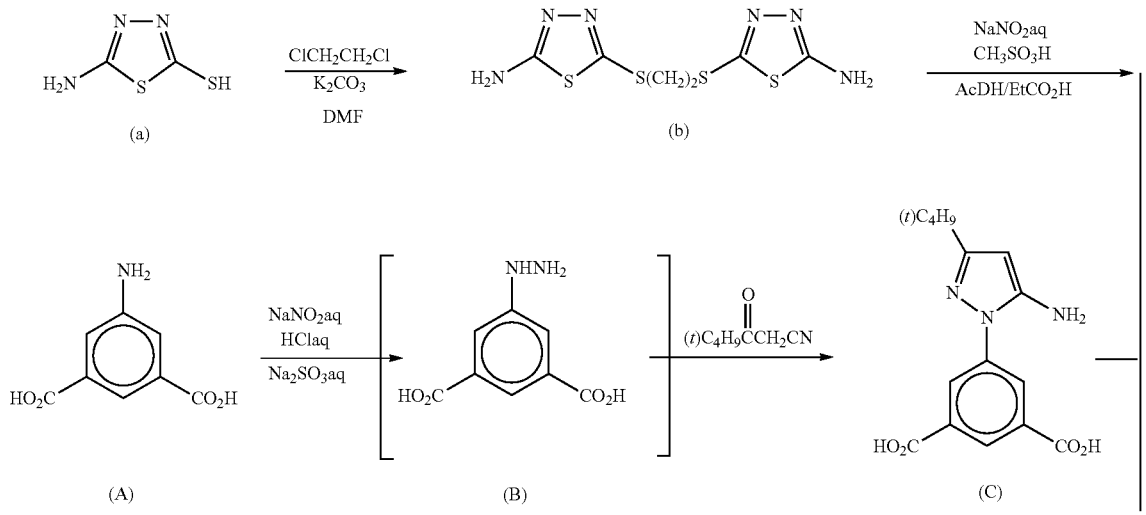

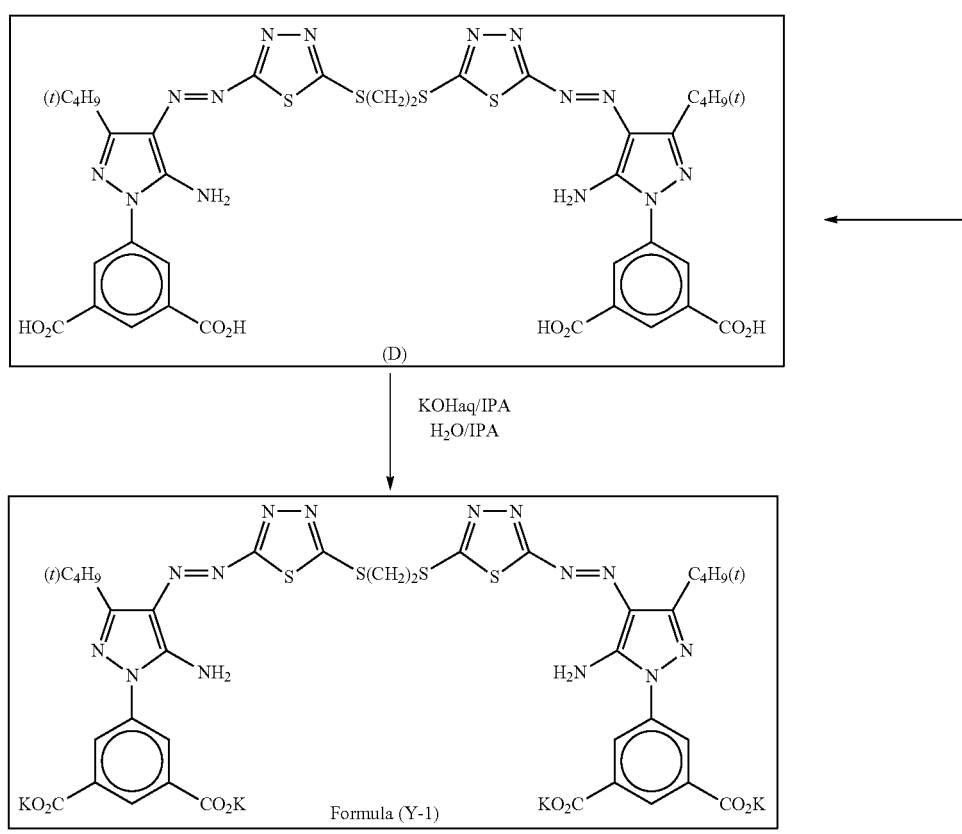

Formula (Y-1)

Synthesis Example 1

76.5 g of a compound (a) (2-amino-5-mercapto-1,3,4-thiadiazole (manufactured by Wako Pure Chemical Industries, Ltd./Catalog no. 019-11125)) was added to 450 mL of DMF (N,N-dimethylformaide) and 24.75 g of 1,2-dichloroethane at room temperature, and 79.5 g of potassium carbonate was added. Thereafter, the temperature was increased up to 70° C., and followed by stirring at the same temperature for 30 minutes. Subsequently, 375 mL of warm water (80° C.) was added dropwise to the reaction solution for 10 minutes, and the internal temperature was cooled to 25° C. The precipitated crystal was separated by filtration, washed with 250 mL of ion-exchanged water, and subsequently with 150 mL of methanol, and dried overnight at 70° C. to obtain 65.1 g of a compound (b).

Synthesis Example 2

181.2 g of amino isophthalic acid (A) (manufactured by Wako Pure Chemical Industries, Ltd./Catalog no. 322-26175)) was suspended in 1000 ml of ion-exchanged water, added with 257 mL of concentrated hydrochloric acid, and maintained in ice bath at 5° C. 116 ml of an aqueous solution of 69.7 g of sodium nitrite was added dropwise thereto (reaction solution A). 1300 ml of an aqueous solution of 378.1 g of sodium sulfite was stirred at the internal temperature of 25° C., and the reaction solution A was added thereto. After stirring for 30 minutes under this state, the internal temperature was heated up to 30° C. Then, after stirring for 60 minutes, 500 mL of hydrochloric acid was added to the reaction solution, and the internal temperature was increased up to 50° C. (reaction solution B). After stirring for 90 minutes under this state, 125.2 g of pivaloylacetonitrile (manufactured by Tokyo Chemical Industry Co., Ltd/Catalog No. P 1112) and 100 mL of isopropanol were added to the reaction solution B, and then, the internal temperature was increased up to 93° C. After stirring for 240 minutes, the resultant product was cooled to room temperature, and a precipitated crystal (C) was filtered by suction, washed with 1500 mL of ion-exchanged water, and subsequently with 1000 mL of isopropanol, and dried (isolated yield: 223.5 g. yield: 73.7%). Synthesis Example 3) 29.2 g of the compound (b) was added to 100 mL of methanesulfonic acid, 120 mL of acetic acid and 180 mL of propionic acid at room temperature, and the internal temperature was increased up to 45° C. to form a homogeneous solution. Then, the internal temperature was cooled to 0° C. Subsequently, a solution of 14.7 g of $NaNO_2$ and 27 mL of ion-exchanged water was added dropwise to the homogeneous solution while maintaining at the internal temperature of 0° C. to 10° C. After stirring at the internal temperature of 5° C. for 15 minutes, a diazonium salt was prepared. The diazonium salt solution was added dropwise to a previously prepared solution of 60.6 g of the coupler component (C) prepared in Synthesis Example 2, 600 mL of methanol and 600 mL of ethylene glycol at a rate maintaining the internal temperature at 0 to 10° C. Subsequently, after stirring at the internal temperature of 25° C. for 30 minutes, a precipitated crystal was filtered and washed with 250 mL of methanol. Then, the crude crystal was dispersed in 650 mL of water, stirred at the internal temperature of 80° C. for 30 minutes, and cooled to room temperature. The resultant product was filtrated, washed with 300 mL of water, and dried at 60° C. overnight to obtain 64.47 g of a colorant (D).

Synthesis Example 4

46.1 g of the colorant (D) prepared in Synthesis Example 3 was added and dissolved in a previously prepared solution of 16.5 g of KOH (tablet) and 414.9 mL of ion-exchanged water at the internal temperature of 20° C. to 30° C.

Subsequently, a solution of 40.0 g of potassium acetate and 200 mL of methanol was added dropwise to the colorant aqueous solution at the internal temperature of 25° C., and followed by stirring at the same temperature for 10 minutes. Next, 2488 mL of IPA (isopropanol) was added dropwise to form a salt. After stirring at the same temperature for 30 minutes, the resultant product was filtered, washed with 500 mL of IPA, and dried at 70° C. overnight to obtain 44 g of a crude crystal of a water soluble dye represented by Formula (Y-1).

Synthesis Example 5

In 78.3 mL of ion-exchanged water, 8.7 g of the crude crystal of the aqueous dye represented by Formula (Y-1) was dissolved at room temperature. Then, the pH value of the aqueous solution was adjusted to 8.5 by using 0.1N hydrochloric acid. After filtration using a membrane filter of 0.2 μm, 391.5 mL of IPA was added dropwise to a filtrate at the internal temperature of 25° C. The precipitated crystal was filtered, washed with 100 mL of IPA, and dried at 80° C. overnight to obtain 7.8 g of a purified crystal of the aqueous dye represented by Formula (Y-1). {λ max: 428 nm ($H_2O$), ε max: $4.20 \times 10^4$}

Synthesis Example 6

7.7 g of a purified crystal of the aqueous dye (Y-2: M=$Na^+$ in Formula (Y)) was obtained in the same manner as in Synthesis Example 4 and Synthesis Example 5 except that NaOH and sodium acetate were used instead of KOH and potassium acetate in Synthesis Example 4, respectively.

Synthesis Example 7

7.4 g of a purified crystal of the aqueous dye (Y-3: M=$Li^+$ in Formula (Y)) was obtained in the same manner as in Synthesis Example 4 and Synthesis Example 5 except that LiOH and lithium acetate were used instead of KOH and potassium acetate in Synthesis Example 4, respectively.

Synthesis Example 8

7.3 g of a purified crystal of the aqueous dye (Y-4: M=$NH_4^+$ in Formula (Y)) was obtained in the same manner as in Synthesis Example 4 and Synthesis Example 5 except that $NH_4OH$ and ammonium acetate were used instead of KOH and potassium acetate in Synthesis Example 4, respectively.

Examples 1 to 40 and Comparative Examples 1 to 14

Preparation of Ink

By using each of the compounds (Y-1) to (Y-4) as the coloring material 1 obtained in Synthesis Examples 5 to 8, each of Compounds 1 to 8 from the Group A as the coloring material 2, and C.I. direct yellow 132 (which is not the coloring material 2), an ink was prepared as described below. First, respective components noted in Tables 3 to 10 below were mixed and sufficiently stirred. Then, through pressure filtration through a filter having a pore size of 0.2 μm, a coloring composition of each of Examples and Comparative Examples was prepared as an ink composition. Also, in the ink, the mass ratio of the content (% by mass) of the second coloring material to the content (% by mass) of the first coloring material ([the content of at least one compound selected from the Group A]/[the content of the compound of Formula (Y) or Formula (Y-1)]) is represented by "coloring material 2/coloring material 1" in Tables 3 to 10 below.

Also, the ink compositions noted in Tables 3 to 10 were added with pH adjusting agents to prepare other ink compositions. The ink compositions before addition of the pH adjusting agents (indicated by Example numbers), the kinds of the pH adjusting agents used for the addition, and the concentrations were noted in Table 12 below.

Also, in Tables 3 to 10, the value of each component indicates % by mass of each component with respect to 100% by mass of the ink composition. Further "balance" indicating the amount of water indicates an amount that makes the total of 100% together with other components except the water.

TABLE 3

| Ink composition | | | | | | | | Unit (%) |
|---|---|---|---|---|---|---|---|---|
| | Examples | | | | | | | |
| | 1 | 2 | 3 | 4 | 5 | 6 | 7 | |
| Coloring material 1 (Y-1) | 2.625 | 2.250 | 2.814 | 2.622 | 2.811 | 2.631 | 2.625 | |
| Coloring material 1 (Y-2) | — | — | — | — | — | — | — | |
| Coloring material 1 (Y-3) | — | — | — | — | — | — | — | |
| Coloring material 1 (Y-4) | — | — | — | — | — | — | — | |
| Coloring material 2 (1 in Group A: M = $K^+$ ion) | 0.0536 | 0.1072 | 0.0109 | 0.0525 | 0.0105 | 0.056 | 0.048 | |
| Coloring material 2 (2 in Group A: M = $K^+$ ion) | 0.1608 | 0.3216 | 0.109 | 0.1575 | 0.105 | 0.168 | 0.144 | |
| Coloring material 2 (3 in Group A: M = $K^+$ ion) | 0.0536 | 0.1072 | 0.0109 | 0.0525 | 0.0105 | 0.0112 | 0.048 | |
| Coloring material 2 (4 in Group A: M = $K^+$ ion) | — | — | — | — | — | — | 0.0096 | |
| Coloring material 2 (5 in Group A: M = $K^+$ ion) | — | — | — | — | — | 0.0112 | 0.0096 | |
| Coloring material 2 (6 in Group A: M = $K^+$ ion) | — | — | — | 0.0105 | 0.0105 | 0.0112 | 0.0096 | |
| Coloring material 2 (7 in Group A: M = $K^+$ ion) | — | — | — | — | — | — | 0.0096 | |
| Coloring material 2 (8 in Group A: M = $K^+$ion) | 0.1072 | 0.2144 | 0.0545 | 0.0105 | 0.0525 | 0.0112 | 0.096 | |
| C.I. Direct Yellow 132 | — | — | — | — | — | — | — | |
| Glycerin | 8 | 8 | 8 | 8 | 8 | 8 | 8 | |
| Diethylene glycol | 8 | 8 | 8 | 8 | 8 | 8 | 8 | |
| Triethylene glycol monobutyl ether | 8 | 8 | 8 | 8 | 8 | 8 | 8 | |
| Acetylenol E 100* | 1 | 1 | 1 | 1 | 1 | 1 | 1 | |

TABLE 3-continued

| | \multicolumn{7}{c}{Ink composition} | Unit (%) |
| | \multicolumn{7}{c}{Examples} | |
| | 1 | 2 | 3 | 4 | 5 | 6 | 7 |
|---|---|---|---|---|---|---|---|
| Pure water | Balance | Balance | Balance | Balance | Balance | Balance | Balance |
| Coloring material 2/Coloring material 1 | 0.143 | 0.333 | 0.066 | 0.144 | 0.067 | 0.140 | 0.143 |

*Surfactant (manufactured by Kawaken Fine Chemicals Co, Ltd.)

TABLE 4

| Ink composition | | | | | | | Unit (%) |
| | \multicolumn{7}{c}{Examples} | |
| | 8 | 9 | 10 | 11 | 12 | 13 | 14 |
|---|---|---|---|---|---|---|---|
| Coloring material 1 (Y-1) | — | — | — | — | — | — | — |
| Coloring material 1 (Y-2) | — | — | — | — | — | — | — |
| Coloring material 1 (Y-3) | 2.625 | 2.250 | 2.814 | 2.622 | 2.811 | 2.631 | 2.625 |
| Coloring material 1 (Y-4) | — | — | — | — | — | — | — |
| Coloring material 2 (1 in Group A: M = $K^+$ ion) | 0.0536 | 0.1072 | 0.0109 | 0.0525 | 0.0105 | 0.056 | 0.048 |
| Coloring material 2 (2 in Group A: M = $K^+$ ion) | 0.1608 | 0.3216 | 0.109 | 0.1575 | 0.105 | 0.168 | 0.144 |
| Coloring material 2 (3 in Group A: M = $K^+$ ion) | 0.0536 | 0.1072 | 0.0109 | 0.0525 | 0.0105 | 0.0112 | 0.048 |
| Coloring material 2 (4 in Group A: M = $K^+$ ion) | — | — | — | — | — | — | 0.0096 |
| Coloring material 2 (5 in Group A: M = $K^+$ ion) | — | — | — | — | — | 0.0112 | 0.0096 |
| Coloring material 2 (6 in Group A: M = $K^+$ ion) | — | — | — | 0.0105 | 0.0105 | 0.0112 | 0.0096 |
| Coloring material 2 (7 in Group A: M = $K^+$ ion) | — | — | — | — | — | — | 0.0096 |
| Coloring material 2 (8 in Group A: M = $K^+$ ion) | 0.1072 | 0.2144 | 0.0545 | 0.105 | 0.0525 | 0.112 | 0.096 |
| C.I. Direct Yellow 132 | — | — | — | — | — | — | — |
| Glycerin | 8 | 8 | 8 | 8 | 8 | 8 | 8 |
| Diethylene glycol | 8 | 8 | 8 | 8 | 8 | 8 | 8 |
| Triethylene glycol monobutyl ether | 8 | 8 | 8 | 8 | 8 | 8 | 8 |
| Acetylenol E 100* | 1 | 1 | 1 | 1 | 1 | 1 | 1 |
| Pure water | Balance | Balance | Balance | Balance | Balance | Balance | Balance |
| Coloring material 2/Coloring material 1 | 0.143 | 0.333 | 0.066 | 0.144 | 0.067 | 0.140 | 0.143 |

*Surfactant (manufactured by Kawaken Fine Chemicals Co, Ltd.)

TABLE 5

| Ink composition | | | | | | | Unit (%) |
| | \multicolumn{7}{c}{Examples} | |
| | 15 | 16 | 17 | 18 | 19 | 20 | 21 |
|---|---|---|---|---|---|---|---|
| Coloring material 1 (Y-1) | — | — | — | 3.0625 | 3.500 | 3.9375 | 4.375 |
| Coloring material 1 (Y-2) | — | — | — | — | — | — | — |
| Coloring material 1 (Y-3) | — | — | — | — | — | — | — |
| Coloring material 1 (Y-4) | 2.625 | 2.622 | 2.631 | — | — | — | — |
| Coloring material 2 (1 in Group A: M = $K^+$ ion) | 0.0536 | 0.0525 | 0.056 | 0.0625 | 0.0714 | 0.0804 | 0.0893 |
| Coloring material 2 (2 in Group A: M = $K^+$ ion) | 0.1608 | 0.1575 | 0.168 | 0.1875 | 0.2142 | 0.2412 | 0.2679 |
| Coloring material 2 (3 in Group A: M = $K^+$ ion) | 0.0536 | 0.0525 | 0.0112 | 0.0625 | 0.0714 | 0.0804 | 0.0893 |
| Coloring material 2 (4 in Group A: M = $K^+$ ion) | — | — | — | — | — | — | — |
| Coloring material 2 (5 in Group A: M = $K^+$ ion) | — | — | 0.0112 | — | — | — | — |
| Coloring material 2 (6 in Group A: M = $K^+$ ion) | — | 0.0105 | 0.0112 | — | — | — | — |
| Coloring material 2 (7 in Group A: M = $K^+$ ion) | — | — | — | — | — | — | — |
| Coloring material 2 (8 in Group A: M = $K^+$ ion) | 0.1072 | 0.105 | 0.112 | 0.125 | 0.1428 | 0.1608 | 0.1786 |
| C.I. Direct Yellow 132 | — | — | — | — | — | — | — |
| Glycerin | 8 | 8 | 8 | 8 | 8 | 8 | 8 |
| Diethylene glycol | 8 | 8 | 8 | 8 | 8 | 8 | 8 |
| Triethylene glycol monobutyl ether | 8 | 8 | 8 | 8 | 8 | 8 | 8 |
| Acetylenol E 100* | 1 | 1 | 1 | 1 | 1 | 1 | 1 |
| Pure water | Balance | Balance | Balance | Balance | Balance | Balance | Balance |
| Coloring material 2/Coloring material 1 | 0.143 | 0.144 | 0.140 | 0.143 | 0.143 | 0.143 | 0.143 |

*Surfactant (manufactured by Kawaken Fine Chemicals Co, Ltd.)

TABLE 6

Ink composition

| | Examples | | | | | | | Unit (%) |
|---|---|---|---|---|---|---|---|---|
| | 22 | 23 | 24 | 25 | 26 | 27 | 28 | |
| Coloring material 1 (Y-1) | 4.8125 | 5.250 | 5.6875 | 2.375 | 2.875 | 3.375 | 3.875 | |
| Coloring material 1 (Y-2) | — | — | — | 2.000 | 1.500 | 1.000 | 0.500 | |
| Coloring material 1 (Y-3) | — | — | — | — | — | — | — | |
| Coloring material 1 (Y-4) | — | — | — | — | — | — | — | |
| Coloring material 2 (1 in Group A: M = $K^+$ ion) | 0.0982 | 0.108 | 0.1138 | 0.0893 | 0.0893 | 0.0893 | 0.0893 | |
| Coloring material 2 (2 in Group A: M = $K^+$ ion) | 0.2946 | 0.324 | 0.3414 | 0.2679 | 0.2679 | 0.2679 | 0.2679 | |
| Coloring material 2 (3 in Group A: M = $K^+$ ion) | 0.0982 | 0.108 | 0.1138 | 0.0893 | 0.0893 | 0.0893 | 0.0893 | |
| Coloring material 2 (4 in Group A: M = $K^+$ ion) | — | — | — | — | — | — | — | |
| Coloring material 2 (5 in Group A: M = $K^+$ ion) | — | — | — | — | — | — | — | |
| Coloring material 2 (6 in Group A: M = $K^+$ ion) | — | — | — | — | — | — | — | |
| Coloring material 2 (7 in Group A: M = $K^+$ ion) | — | — | — | — | — | — | — | |
| Coloring material 2 (8 in Group A: M = $K^+$ ion) | 0.1964 | 0.216 | 0.2276 | 0.1786 | 0.1786 | 0.1786 | 0.1786 | |
| C.I. Direct Yellow 132 | — | — | — | — | — | — | — | |
| Glycerin | 8 | 8 | 8 | 8 | 8 | 8 | 8 | |
| Diethylene glycol | 8 | 8 | 8 | 8 | 8 | 8 | 8 | |
| Triethylene glycol monobutyl ether | 8 | 8 | 8 | 8 | 8 | 8 | 8 | |
| Acetylenol E 100* | 1 | 1 | 1 | 1 | 1 | 1 | 1 | |
| Pure water | Balance | Balance | Balance | Balance | Balance | Balance | Balance | |
| Coloring material 2/Coloring material 1 | 0.143 | 0.144 | 0.140 | 0.143 | 0.143 | 0.143 | 0.143 | |

*Surfactant (manufactured by Kawaken Fine Chemicals Co, Ltd.)

TABLE 7

Ink composition

| | Examples | | | | | | | Unit (%) |
|---|---|---|---|---|---|---|---|---|
| | 29 | 30 | 31 | 32 | 33 | 34 | 35 | |
| Coloring material 1 (Y-1) | 3.000 | 3.000 | 3.000 | 3.000 | 3.000 | 3.000 | 3.000 | |
| Coloring material 1 (Y-2) | — | — | — | — | — | — | — | |
| Coloring material 1 (Y-3) | — | — | — | — | — | — | — | |
| Coloring material 1 (Y-4) | — | — | — | — | — | — | — | |
| Coloring material 2 (1 in Group A: M = $K^+$ ion) | 0.0043 | 0.0073 | 0.0143 | 0.0214 | 0.086 | 0.1429 | 0.214 | |
| Coloring material 2 (2 in Group A: M = $K^+$ ion) | 0.0129 | 0.0219 | 0.0429 | 0.0642 | 0.258 | 0.4287 | 0.642 | |
| Coloring material 2 (3 in Group A: M = $K^+$ ion) | 0.0043 | 0.0073 | 0.0143 | 0.0214 | 0.086 | 0.1429 | 0.214 | |
| Coloring material 2 (4 in Group A: M = $K^+$ ion) | — | — | — | — | — | — | — | |
| Coloring material 2 (5 in Group A: M = $K^+$ ion) | — | — | — | — | — | — | — | |
| Coloring material 2 (6 in Group A: M = $K^+$ ion) | — | — | — | — | — | — | — | |
| Coloring material 2 (7 in Group A: M = $K^+$ ion) | — | — | — | — | — | — | — | |
| Coloring material 2 (8 in Group A: M = $K^+$ ion) | 0.0086 | 0.0146 | 0.0286 | 0.0428 | 0.172 | 0.2858 | 0.428 | |
| C.I. Direct Yellow 132 | — | — | — | — | — | — | — | |
| Glycerin | 8 | 8 | 8 | 8 | 8 | 8 | 8 | |
| Diethylene glycol | 8 | 8 | 8 | 8 | 8 | 8 | 8 | |
| Triethylene glycol monobutyl ether | 8 | 8 | 8 | 8 | 8 | 8 | 8 | |
| Acetylenol E 100* | 1 | 1 | 1 | 1 | 1 | 1 | 1 | |
| Pure water | Balance | Balance | Balance | Balance | Balance | Balance | Balance | |
| Coloring material 2/Coloring material 1 | 0.01 | 0.017 | 0.033 | 0.050 | 0.200 | 0.333 | 0.500 | |

*Surfactant (manufactured by Kawaken Fine Chemicals Co, Ltd.)

TABLE 8

Ink composition

| | Examples | | | | | Unit (%) |
|---|---|---|---|---|---|---|
| | 36 | 37 | 38 | 39 | 40 | |
| Coloring material 1 (Y-1) | 2.125 | 2.025 | 2.025 | 1.925 | 2.325 | |
| Coloring material 1 (Y-2) | 0.5 | 0.5 | 0.5 | 0.5 | 0.1 | |
| Coloring material 1 (Y-3) | — | 0.1 | — | 0.1 | 0.1 | |
| Coloring material 1 (Y-4) | — | — | 0.1 | 0.1 | 0.1 | |

TABLE 8-continued

Ink composition

| | Examples | | | | | Unit (%) |
|---|---|---|---|---|---|---|
| | 36 | 37 | 38 | 39 | 40 | |
| Coloring material 2 (1 in Group A: M = K$^+$ ion) | 0.0536 | 0.0536 | 0.0536 | 0.0536 | 0.0536 | |
| Coloring material 2 (2 in Group A: M = K$^+$ ion) | 0.1608 | 0.1608 | 0.1608 | 0.1608 | 0.1608 | |
| Coloring material 2 (3 in Group A: M = K$^+$ ion) | 0.0536 | 0.0536 | 0.0536 | 0.0536 | 0.0536 | |
| Coloring material 2 (4 in Group A: M = K$^+$ ion) | — | — | — | — | — | |
| Coloring material 2 (5 in Group A: M = K$^+$ ion) | — | — | — | — | — | |
| Coloring material 2 (6 in Group A: M = K$^+$ ion) | — | — | — | — | — | |
| Coloring material 2 (7 in Group A: M = K$^+$ ion) | — | — | — | — | — | |
| Coloring material 2 (8 in Group A: M = K$^+$ ion) | 0.1072 | 0.1072 | 0.1072 | 0.1072 | 0.1072 | |
| C.I. Direct Yellow 132 | — | — | — | — | — | |
| Glycerin | 8 | 8 | 8 | 8 | 8 | |
| Diethylene glycol | 8 | 8 | 8 | 8 | 8 | |
| Triethylene glycol monobutyl ether | 8 | 8 | 8 | 8 | 8 | |
| Acetylenol E 100* | 1 | 1 | 1 | 1 | 1 | |
| Pure water | Balance | Balance | Balance | Balance | Balance | |
| Coloring material 2/Coloring material 1 | 0.143 | 0.143 | 0.143 | 0.143 | 0.143 | |

*Surfactant (manufactured by Kawaken Fine Chemicals Co, Ltd.)

TABLE 9

Ink composition

| | Comparative Examples | | | | | | | Unit (%) |
|---|---|---|---|---|---|---|---|---|
| | 1 | 2 | 3 | 4 | 5 | 6 | 7 | |
| Coloring material 1 (Y-1) | — | — | 2.0 | 3.0 | 3.0 | 3.0 | 3.0 | |
| Coloring material 1 (Y-2) | — | — | 2.0 | — | — | — | 0.05 | |
| Coloring material 1 (Y-3) | — | — | — | — | — | — | — | |
| Coloring material 1 (Y-4) | — | — | — | — | — | — | — | |
| Coloring material 2 (1 in Group A: M = K$^+$ ion) | — | — | — | — | — | — | — | |
| Coloring material 2 (2 in Group A: M = K$^+$ ion) | — | — | — | — | — | 0.0005 | 0.0005 | |
| Coloring material 2 (3 in Group A: M = K$^+$ ion) | — | — | — | — | — | 0.0005 | 0.0005 | |
| Coloring material 2 (4 in Group A: M = K$^+$ ion) | — | — | — | — | — | — | — | |
| Coloring material 2 (5 in Group A: M = K$^+$ ion) | — | — | — | — | — | — | — | |
| Coloring material 2 (6 in Group A: M = K$^+$ ion) | — | — | — | — | 0.0015 | 0.0005 | 0.0005 | |
| Coloring material 2 (7 in Group A: M = K$^+$ ion) | — | — | — | — | — | — | — | |
| C.I. Direct Yellow 132 | 3.0 | 4.0 | — | 0.3 | 0.15 | 0.15 | 0.1 | |
| Glycerin | 8.00 | 8.00 | 8.00 | 8.00 | 8.00 | 8.00 | 8.00 | |
| Diethylene glycol | 8.00 | 8.00 | 8.00 | 8.00 | 8.00 | 8.00 | 8.00 | |
| Triethylene glycol monobutyl ether | 8.00 | 8.00 | 8.00 | 8.00 | 8.00 | 8.00 | 8.00 | |
| Acetylenol E 100* | 1.00 | 1.00 | 1.00 | 1.00 | 1.00 | 1.00 | 1.00 | |
| Pure water | Balance | Balance | Balance | Balance | Balance | Balance | Balance | |
| Coloring material 2/Coloring material 1 | — | — | — | — | 0.0005 | 0.0005 | 0.00049 | |

*Surfactant (manufactured by Kawaken Fine Chemicals Co, Ltd.)

TABLE 10

Ink composition

| | Comparative Examples | | | | | | | Unit (%) |
|---|---|---|---|---|---|---|---|---|
| | 8 | 9 | 10 | 11 | 12 | 13 | 14 | |
| Coloring material 1 (Y-1) | 1.0 | — | 1.0 | 1.02 | 1.0 | 0.5 | 1.0 | |
| Coloring material 1 (Y-2) | — | 1.0 | — | — | — | 0.5 | 1.0 | |
| Coloring material 1 (Y-3) | — | — | — | — | — | — | — | |
| Coloring material 1 (Y-4) | — | — | — | — | — | — | — | |
| Coloring material 2 (1 in Group A: M = K$^+$ ion) | — | — | — | — | — | — | — | |
| Coloring material 2 (2 in Group A: M = K$^+$ ion) | — | — | — | 0.66 | 0.50 | 0.5 | 1.0 | |
| Coloring material 2 (3 in Group A: M = K$^+$ ion) | 2.0 | 2.0 | 1.0 | 0.66 | 0.50 | 0.5 | 1.0 | |
| Coloring material 2 (4 in Group A: M = K$^+$ ion) | — | — | — | — | — | — | — | |
| Coloring material 2 (5 in Group A: M = K$^+$ ion) | — | — | — | — | 0.50 | 0.5 | 1.0 | |

TABLE 10-continued

Ink composition

| | Comparative Examples | | | | | | | Unit (%) |
|---|---|---|---|---|---|---|---|---|
| | 8 | 9 | 10 | 11 | 12 | 13 | 14 | |
| Coloring material 2 (6 in Group A: M = K⁺ ion) | — | — | 1.0 | 0.66 | 0.50 | 0.5 | 1.0 | |
| Coloring material 2 (7 in Group A: M = K⁺ ion) | — | — | — | — | — | — | — | |
| C.I. Direct Yellow 132 | — | — | — | — | — | — | — | |
| Glycerin | 8.00 | 8.00 | 8.00 | 8.00 | 8.00 | 8.00 | 8.00 | |
| Diethylene glycol | 8.00 | 8.00 | 8.00 | 8.00 | 8.00 | 8.00 | 8.00 | |
| Triethylene glycol monobutyl ether | 8.00 | 8.00 | 8.00 | 8.00 | 8.00 | 8.00 | 8.00 | |
| Acetylenol E 100* | 1.00 | 1.00 | 1.00 | 1.00 | 1.00 | 1.00 | 1.00 | |
| Pure water | Balance | Balance | Balance | Balance | Balance | Balance | Balance | |
| Coloring material 2/Coloring material 1 | 2.00 | 2.00 | 2.00 | 1.94 | 2.00 | 2.00 | 2.00 | |

*Surfactant (manufactured by Kawaken Fine Chemicals Co, Ltd.)

<Evaluation>
(1) Light Fastness

The ink obtained from each of Examples 1 to 40 and Comparative Examples 1 to 14 was mounted in an inkjet recording device (trade name: PIXUS iP8600; manufactured by Canon) using heat energy. The recording condition was set as follows: temperature 23° C., RH 55%, recording density 2,400 dpi×1,200 dpi, and discharge amount 2.5 pL.

On a recording medium (trade name: Canon photo paper glossy pro [platinum grade] PT-101; manufactured by Canon), an image was formed at a recording duty of 50%. The image was air-dried at the temperature of 23° C. and 55% RH for 24 hours. On the image portion of a recorded matter obtained through this process, an optical density was measured (referred to as "optical density before the test"). Also, this recorded matter was exposed using a super Xenon tester (trade name: SX-75; manufactured by Suga Test Co., Ltd.), under conditions of irradiation intensity 100 kilo lux, bath internal temperature 24° C., and RH 60% for 72 hours. Then, on the image portion of the record matter, an optical density was measured ("optical density after the test"). Also, the optical density was measured using a spectrophotometer (Spectorolino; manufactured by Gretag Macbeth) under conditions of light source D50 and field of view 2°. From the obtained optical density values before and after the test, a residual ratio of the optical density was calculated based on the following equation, and evaluation of light fastness was performed.

The light fastness was based on the following criteria. The evaluation result is noted in Table 11.

In the present invention, in the following criteria, AA and A were set as acceptable levels, and B and C were set as unacceptable levels.

$$\text{Residual ration of optical density [\%]} = \frac{\text{Optical density after test}}{\text{Optical density before test}} \times 100 \ [\%]$$

AA: residual ratio of optical density of 90% or more.
A: residual ratio of optical density of 80% or more and less than 90%.
B: residual ratio of optical density of 70% or more and less than 80%.
C: residual ratio of optical density of less than 70%.
(2) Hue The ink obtained from each of Examples 1 to 40 and Comparative Examples 1 to 14 was mounted in an inkjet recording device using heat energy (trade name: PIXUS iP8600; manufactured by Canon). The recording condition was set as follows: temperature 23° C., RH 55%, recording density 2,400 dpi×1,200 dpi, and discharge amount 2.5 pL. Then, on the same recording medium as that above, an image was formed at a recording duty of 60%. The image was air-dried at the temperature of 23° C. and 55% RH for 24 hours. On the image portion of a recorded matter obtained through this process, a hue angle was measured using a spectrophotometer (Spectorolino; manufactured by Gretag Macbeth), and evaluation of a hue was performed. The hue was based on the following criteria. The evaluation result is noted in Table 11. In the present invention, in the following criteria, AA, A, and B were set as acceptable levels, and C was set as an unacceptable level.

AA: hue angle of 88° or more and 90° or less.
A: hue angle of 85° or more and less than 88°, or greater than 90° and 92° or less.
B: hue angle of 83° or more and less than 85°, or greater than 92° and 94° or less.
C: hue angle of less than 83°, or greater than 94°.
(3) Storage Stability of Ink The ink obtained from each of Examples 1 to 40 and Comparative Examples 1 to 14 was filled in an ink cartridge for an inkjet recording device (trade name: PIXUS iP8600; manufactured by Canon), and an ink supply hole was closed so that the ink within the ink cartridge may be not evaporated. The ink cartridge was put in an airtight container, and stored in a thermostatic oven at the temperature of 60° C. for 3 months. Then, the ink cartridge was taken out from the thermostatic oven, and mounted in a head cartridge of the inkjet recording device, and then stored at the temperature of 35° C. and RH 10% for 2 weeks in the state where discharge holes of the head cartridge were exposed. Then, the head cartridge was mounted in the inkjet recording device as above, and subjected to suction predetermined times, so as to determine restorability. In this manner, evaluation of storage stability of the ink was performed. Also, the suction is one of functions provided to the inkjet recording device (trade name: PIXUS iP8600; manufactured by Canon), which is, "cleaning of print head". The storage stability was based on the following criteria. The evaluation result is noted in Table 11. In the present invention, in the following criteria, AA and A were set as acceptable levels, and B and C were set as unacceptable levels.

AA: all of discharge holes were restored to a state where discharge can be carried out without a problem after suction 4 or less times.

A: all of discharge holes were restored to a state where discharge can be carried out without a problem after suction 5 times.

B: all of discharge holes were restored to a state where discharge can be carried out without a problem after suction 6 times.

C: discharge holes through which discharge cannot be carried out even after suction 7 or more times.

(4) Recording Durability

The ink obtained from each of Examples 1 to 40 and Comparative Examples 1 to 14 was mounted in a position of a yellow ink of an inkjet recording device using heat energy (trade name: BJ F890; manufactured by Canon). Then, on the whole surface of a recording medium with an A4 size (trade name: Office Planner: manufactured by Canon), an image was recorded at a recording duty of 100%, and evaluation of recording durability was performed. The recording durability was based on the following criteria. The evaluation result is noted in Table 11. In the present invention, in the following criteria, AA and A were set as acceptable levels, and B and C were set as unacceptable levels.

AA: twist or blur did not occur even after recording of 20,000 sheets.

A: slight blur occurred due to minute twist after recording of 15,000 to 19,999 sheets.

B: slight blur occurred due to minute twist after recording of 10,000 to 14,999 sheets.

C: blur occurred or non-discharge occurred due to disconnection before recording of less than 10,000.

(5) pH Stability of Ink

The pH of the ink obtained from each of Examples 1 to 35 was measured using a pH meter (HM-30G (manufactured by DKK-TOA Corp.), electrode: combination electrode GST-5721C, temperature: 25° C.). After pH measurement, the storage stability test described in (3) was performed. After the test, the pH was measured again.

Also, the inks of Examples 41 to 61, obtained by adding the pH adjusting agents noted in Table 12 to the inks of Examples 1 to 35 were subjected to the same measurement. In the present invention, in the following criteria, AA, A, and B were set as acceptable levels, and C was set as an unacceptable level.

AA: pH difference between before and after the test pH is less than 0.10

A: pH difference between before and after the test pH is 0.10 or more and less than 0.15

B: pH difference between before and after the test pH is 0.15 or more and less than 0.20

C: pH difference between before and after the test pH is 0.20 or more

TABLE 11

| | Evaluation result | | | |
|---|---|---|---|---|
| | Light fastness | Hue | Storage stability | Recording durability |
| Example 1 | A | AA | AA | AA |
| Example 2 | A | AA | AA | AA |
| Example 3 | A | AA | AA | AA |
| Example 4 | A | AA | AA | AA |
| Example 5 | A | AA | AA | AA |
| Example 6 | A | AA | AA | AA |
| Example 7 | A | AA | AA | AA |
| Example 8 | A | AA | A | A |
| Example 9 | A | AA | A | A |
| Example 10 | A | AA | A | A |
| Example 11 | A | AA | A | A |
| Example 12 | A | AA | A | A |
| Example 13 | A | AA | A | A |
| Example 14 | A | AA | A | A |
| Example 15 | A | AA | A | A |
| Example 16 | A | AA | A | A |
| Example 17 | A | AA | A | A |
| Example 18 | A | AA | AA | AA |
| Example 19 | AA | AA | AA | AA |
| Example 20 | AA | AA | AA | AA |
| Example 21 | AA | AA | AA | AA |
| Example 22 | AA | AA | AA | AA |
| Example 23 | AA | AA | AA | AA |
| Example 24 | AA | AA | AA | AA |
| Example 25 | A | AA | A | A |
| Example 26 | A | AA | A | A |
| Example 27 | A | AA | A | A |
| Example 28 | A | AA | A | A |
| Example 29 | A | AA | AA | AA |
| Example 30 | A | AA | AA | AA |
| Example 31 | A | AA | AA | AA |
| Example 32 | A | AA | AA | AA |
| Example 33 | A | A | AA | AA |
| Example 34 | A | A | AA | AA |
| Example 35 | A | A | AA | AA |
| Example 36 | A | A | A | A |
| Example 37 | A | A | A | A |
| Example 38 | A | A | A | A |
| Example 39 | A | A | A | A |
| Example 40 | A | A | A | A |
| Comp. Example 1 | C | A | A | A |
| Comp. Example 2 | C | A | A | A |
| Comp. Example 3 | A | AA | B | B |
| Comp. Example 4 | C | A | A | A |
| Comp. Example 5 | B | A | A | A |
| Comp. Example 6 | B | A | A | A |
| Comp. Example 7 | B | A | A | A |
| Comp. Example 8 | A | A | B | B |
| Comp. Example 9 | A | A | B | B |
| Comp. Example 10 | A | A | B | B |
| Comp. Example 11 | A | A | B | B |
| Comp. Example 12 | A | A | B | B |
| Comp. Example 13 | A | A | B | B |
| Comp. Example 14 | A | A | B | B |

TABLE 12

| | Evaluation result | | | | |
|---|---|---|---|---|---|
| Ink | pH Stability | Ink | pH adjusting agent | Concentration of pH adjusting agent*/wt % | pH Stability |
| Example 1 | A | Example 41 | Potassium hydrogen carbonate | 0.14 | AA |
| Example 2 | A | Example 42 | Potassium hydrogen carbonate | 0.21 | AA |
| Example 3 | A | Example 43 | Potassium hydrogen carbonate | 0.07 | AA |
| Example 4 | A | Example 44 | Potassium hydrogen carbonate | 0.14 | AA |
| Example 5 | A | Example 45 | Potassium hydrogen carbonate | 0.70 | AA |
| Example 6 | A | Example 46 | Potassium hydrogen carbonate | 0.14 | AA |

TABLE 12-continued

Evaluation result

| Ink | pH Stability | Ink | pH adjusting agent | Concentration of pH adjusting agent*/wt % | pH Stability |
|---|---|---|---|---|---|
| Example 7 | A | Example 47 | Potassium carbonate | 0.07 | AA |
| Example 18 | A | Example 48 | Potassium hydrogen carbonate | 0.14 | AA |
| Example 19 | B | Example 49 | Potassium hydrogen carbonate | 0.14 | AA |
| Example 20 | B | Example 50 | Potassium hydrogen carbonate | 0.14 | AA |
| Example 21 | A | Example 51 | Potassium hydrogen carbonate | 0.14 | AA |
| Example 22 | B | Example 52 | Potassium hydrogen carbonate | 0.70 | A |
| Example 23 | B | Example 53 | Potassium hydrogen carbonate | 0.70 | A |
| Example 24 | A | Example 54 | Potassium hydrogen carbonate | 0.14 | AA |
| Example 29 | A | Example 55 | Potassium carbonate | 0.07 | AA |
| Example 30 | A | Example 56 | Potassium carbonate | 0.07 | AA |
| Example 31 | A | Example 57 | Potassium carbonate | 0.07 | AA |
| Example 32 | B | Example 58 | Potassium hydrogen carbonate | 0.14 | AA |
| Example 33 | A | Example 59 | Potassium hydrogen carbonate | 0.35 | A |
| Example 34 | A | Example 60 | Potassium hydrogen carbonate | 0.14 | AA |
| Example 35 | A | Example 61 | Potassium hydrogen carbonate | 0.14 | AA |

Although the inks in Examples 8 to 17, Examples 25 to 28, and Examples 36 to 40 were ranked A in evaluations on both the storage stability of an ink and the recording durability, it was determined that the inks in Examples 1 to 7, Examples 18 to 24, and Examples 29 to 35 were superior because the counteraction in an ionic hydrophilic group is a single $K^+$ ion system.

Also, although the inks in Examples 1 to 18 and Examples 25 to 40 were ranked A in evaluation on the light fastness of a recording image, it was determined that the inks in Examples 19 to 24 were superior in the grade of the light fastness because the content (% by mass) of the first coloring material is high in each of the inks.

Also, although all of the inks in Examples 33 to 40 were ranked A in evaluation on the hue of a recording image, the inks in Examples 1 to 32 were superior in the grade of the hue because the content (% by mass) of the second coloring material is low in each of the inks.

All of the inks of Examples 41 to 61, obtained by adding the pH adjusting agents to the inks of Examples 1 to 35, were ranked AA or A in the pH stability. Thus, it was determined that the pH stability was improved as compared to the inks not added with the pH adjusting agents in Examples 1 to 35.

From the results in Table 11 and 12, it can be found that the system using the coloring composition (the ink for inkjet recording) of the present invention is superior in light fastness, hue, storage stability of an ink, recording durability of an ink, pH stability of an ink of an inkjet recording image.

INDUSTRIAL APPLICABILITY

The coloring composition and the azo compound of the present invention may provide an image excellent in preservation properties (especially, light fastness, ozone gas fastness and moisture fastness), and form an image excellent in hue, and at the same time may suppress clogging of an ink supply path or sufficiently satisfy storage stability.

The present invention has been described in detail with reference to specific embodiments, but it is apparent to the person with ordinary skill in the art that various changes or modifications may be made without departing from the spirit and the scope of the present invention.

This application is based on Japanese Patent Application Nos. 2010-294320 and 2011-142323 filed on Dec. 28, 2010 and Jun. 27, 2011, respectively in the JPO, the disclosure of which is incorporated herein by reference in its entirety

The invention claimed is:

1. A coloring composition comprising at least a first coloring material and at least a second coloring material,
   wherein the first coloring material is a compound represented by the Formula (Y),
   the second coloring material is at least one compound selected from the group A, and
   a mass ratio of a content of the second coloring material in the composition to a content of the first coloring material in the composition is 0.001 to 1.0:

Formula (Y)

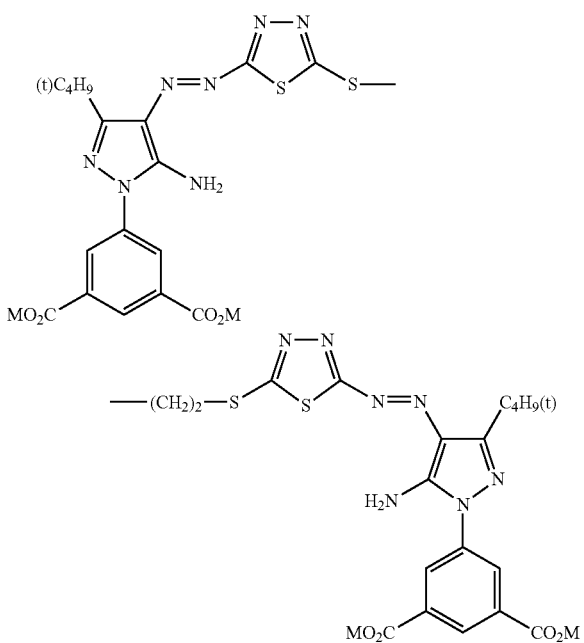

wherein in Formula (Y), a plurality of M each independently represent a hydrogen atom or a cation, and when M represents a cation, M represents a $Li^+$ ion, a $Na^+$ ion, a $K^+$ ion or a $NH_4^+$ ion:

Group A

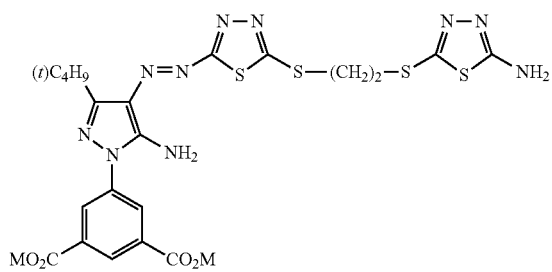
1

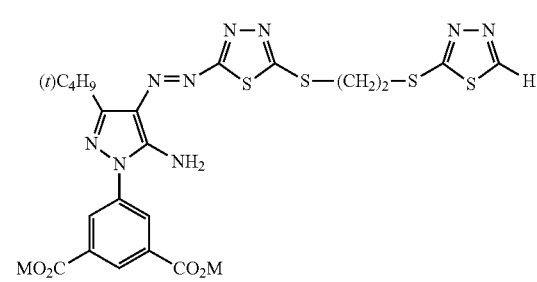
2

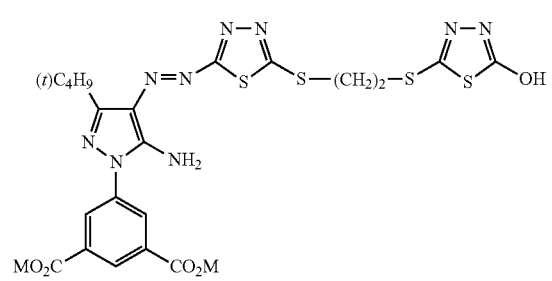
3

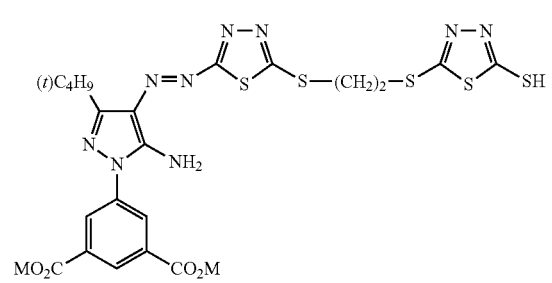
4

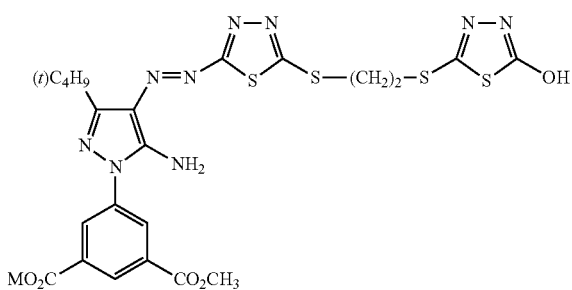
5

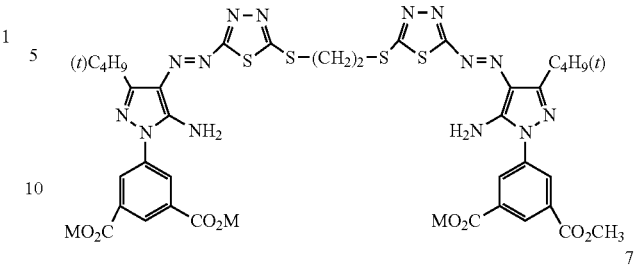
6

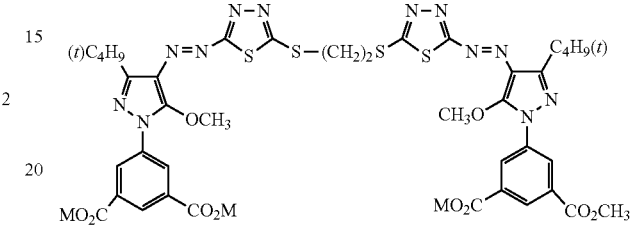
7

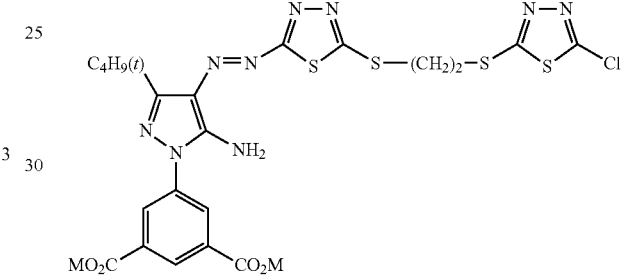
8 wherein in Group A, a plurality of M each independently represent a hydrogen atom or a cation, and when M represents a cation, M represents a Li$^+$ ion, a Na$^+$ ion, a K$^+$ ion or a NH$_4^+$ ion.

2. The coloring composition of claim 1, wherein the compound selected from the Group A is at least one kind selected from compounds 1, 2, 3 and 8.

3. The coloring composition of claim 1, wherein a main component of M is a K$^+$ ion in the compound represented by Formula (Y), and a main component of M is a K$^+$ ion in the compound selected from the Group A.

4. The coloring composition of claim 1, wherein M is a K$^+$ ion in both of the compound represented by Formula (Y) and the compound selected from Group A.

5. The coloring composition of claim 1, wherein a content of the first coloring material is 1% by mass to 15% by mass based on a total mass of the coloring composition.

6. The coloring composition of claim 1, wherein a content of the first coloring material is 8% by mass to 12% by mass based on a total mass of the coloring composition.

7. The coloring composition of claim 1, wherein a mass ratio of a content of the second coloring material in the coloring composition to a content of the first coloring material in the coloring composition is 0.001 to 0.2.

8. The coloring composition of claim 1, wherein a content of the second coloring material is 0.01% by mass to 1.1% by mass based on a total mass of the coloring composition.

9. An ink comprising the coloring composition of claim 1.

* * * * *